(12) United States Patent
Marlow et al.

(10) Patent No.: US 11,428,695 B2
(45) Date of Patent: Aug. 30, 2022

(54) CONCENTRATION-DEPENDENT SELF-INTERACTION ASSAY

(71) Applicant: Regeneron Pharmaceuticals, Inc., Tarrytown, NY (US)

(72) Inventors: Michael Marlow, New Rockelle, NY (US); Michael Sennett, Sommerville, MA (US); Michael Schneider, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 16/326,238

(22) PCT Filed: Aug. 18, 2017

(86) PCT No.: PCT/US2017/047630
§ 371 (c)(1),
(2) Date: Feb. 18, 2019

(87) PCT Pub. No.: WO2018/035470
PCT Pub. Date: Feb. 22, 2018

(65) Prior Publication Data
US 2019/0187149 A1 Jun. 20, 2019

Related U.S. Application Data

(60) Provisional application No. 62/376,788, filed on Aug. 18, 2016.

(51) Int. Cl.
*G01N 33/68* (2006.01)
*G01N 33/58* (2006.01)
(Continued)

(52) U.S. Cl.
CPC ......... *G01N 33/6845* (2013.01); *G01N 21/77* (2013.01); *G01N 33/587* (2013.01)

(58) Field of Classification Search
CPC .. G01N 21/314; G01N 33/6845; G01N 21/77; G01N 33/587
See application file for complete search history.

(56) References Cited

U.S. PATENT DOCUMENTS 4,080,264 A 3/1978 Cohen et al.
7,087,411 B2 8/2006 Daly et al.
(Continued)

FOREIGN PATENT DOCUMENTS

AU 2017313150 A1 2/2019
BR 112019003175 A2 6/2019
(Continued)

OTHER PUBLICATIONS

Geng et al. ("Facile Preparation of Stable Antibody-Gold Conjugates and Application to Affinity-Capture Self-Interaction Nanoparticle Spectroscopy," Bioconjugate Chem. 2016, vol. 27, pp. 2287-2300, published Aug. 5, 2016) (Year: 2016).*

(Continued)

*Primary Examiner* — Tracy Vivlemore
*Assistant Examiner* — Nam P Nguyen
(74) *Attorney, Agent, or Firm* — McCarter & English, LLP

(57) ABSTRACT

Methods for producing high concentration protein formulations having high stability are provided. Assays for selecting proteins and formulation conditions that have high self-repulsive attributes are used as an early step in the manufacturing process. Specifically, a protein concentration-dependent self-interaction nanoparticle spectroscopy method is employed as a protein colloidal interaction assay.

18 Claims, 17 Drawing Sheets

(51) Int. Cl.
  *G01N 21/31* (2006.01)
  *G01N 21/77* (2006.01)

(56) References Cited

U.S. PATENT DOCUMENTS

| | | | |
|---|---|---|---|
| 7,514,938 B2 | 4/2009 | Publicover et al. |
| 7,771,997 B2 | 8/2010 | Chen et al. |
| 7,927,583 B2 | 4/2011 | Stahl et al. |
| 2007/0291265 A1 | 12/2007 | Holman |
| 2011/0305765 A1 | 12/2011 | Mathur et al. |
| 2016/0074515 A1 | 3/2016 | Soane et al. |
| 2016/0123968 A1 | 5/2016 | Iida et al. |

FOREIGN PATENT DOCUMENTS

| | | |
|---|---|---|
| CA | 3032361 A1 | 2/2018 |
| CN | 101022831 A | 8/2007 |
| CN | 101522219 A | 9/2009 |
| CN | 104062287 A | 9/2014 |
| CN | 109661577 A | 4/2019 |
| EA | 201990316 A1 | 7/2019 |
| EP | 3500856 A1 | 6/2019 |
| JP | 2019-532267 A | 11/2019 |
| KR | 2019-0039185 A | 4/2019 |
| MX | 2019001930 A | 7/2019 |
| SG | 11201900895 | 2/2019 |
| WO | 2014/192937 A1 | 12/2014 |
| WO | 2016/070050 A1 | 5/2016 |
| WO | 2016115475 | 7/2016 |
| WO | 2016115475 A1 | 7/2016 |
| WO | 2018/035470 A1 | 2/2018 |

OTHER PUBLICATIONS

Intention to grant for EP application No. 17761159.7 dated Jun. 5, 2020, 6 pages.
International Preliminary Reporton Patentability received for PCT Patent Application No. PCT/US17/047630, dated Feb. 28, 2019, 7 pages.
International Search Report and Written Opinion received for PCT Patent Application No. PCT/US17/047630, dated Oct. 4, 2017, 9 pages.
Office Action received for European Application No. 17761159, dated Feb. 24, 2020, 6 pages.
Co-Pending European Patent Application No. 17761159.7, Communication under Rule 71(3) EPC (notice of allowance) dated Jun. 5, 2020.
Liu, Yuwen, et al., "RNA-seq Differential Expression Studies: More Sequence or More Replication?", Bioinformatics Discovery Note, vol. 30 No. 3, pp. 301-304 (2014).
Invitation to Respond to Written Opinion released by the Intellectual Property Office of Singapore in co-pending application No. 11201900895Q dated Jul. 24, 2020; 7 pages.
Blixt, et al., "Arraying the post-translational glycoproteome (PTG)," Curr Opin Chem Bio, 18:62-69 (2014).

Geng, et al., "Improving Monoclonal Antibody Selection and Engineering using Measurements of Colloidal Protein Interactions," J Pharm Sci, 103(11):3356-3363 (2014).
Geng, et al., "Facile Preparations of Stable Antibody-Gold Conjugates and Application to Affinity-Capture Self-Interaction Nanoparticle Spectroscopy," Bioconjugate Chem, 27(10):2287-2300 (2016 ).
Geng, et al., "Measurements of Monoclonal Antibody Self-Association are Correlated with Complex Biophysical Properties," Mol Pharm, 13(5):1636-1645 (2016).
Geohegan, et al., "Mitigation of reversible self-association and viscosity in a human IgG1 monoclonal antibody by rational, structure-guided Fv engineering," mAbs, 8(5):941-950 (2016).
Ghaderi, et al., "Production platforms for biotherapeutic glycoproteins, Occurrence, impact, and challenges of non-human sialylation," Biotech Genet Eng Rev, 28:147-75 (2012).
Huang, C., "Receptor-Fc fusion therapeutics, traps, and MIMETIBODY technology," Curr Opin Biotech, 20(6):692-9 (2009).
Lukham, et al., "Effect of Particle Size Distribution on the Rheology of Dispersed Systems," J. Colloid Interface Sci, 220(2):347-356 (1999).
Mowen, et al., "Unconventional post-translational modifications in immunological signaling," Nat Immun, 15(6):512-20 (2014).
Oka, et al., "Forming disulfides in the endoplasmic reticulum," Biochem Biophys Acta 1833:2425-2429 (2013).
Pathak, et al., "Do Clustering Monoclonal Antibody Solutions Really Have a Concentration Dependence of Viscosity?" Biophys J. 104(4):913-923 (2013).
Shire, S., "Formulation and Manufacturability of Biologies," Curr Opin Biotech 20(6):708-14 (2009).
Sule, et al., "High-Throughput Analysis of Concentration Dependent Antibody Self-Association," Biophys Jour, 101:1749-1757 (2011).
Sule, et al., "Solution pH That Minimizes Self-Association of Three Monoclonal Antibodies Is Strongly Dependent on Ionic Strength," Mol Pharm, 9(4):744-751 (2012).
Sule, et al., "Rapid Analysis of Antibody Self-Association in Complex Mixtures Using Immunogold Conjugates," Mol Pharm, 10:1322-1331 (2013).
Tessier, et al., "Self-Interaction Nanoparticle Spectroscopy: A Nanoparticle-Based Protein Interaction Assay," J. Amer Chem Soc, 130(10):3106-3112 (2008).
Wu, J, et al., "Discovery of highly soluble antibodies prior to purification using affinity-capture self-interaction nanoparticle spectroscopy," Prot Eng Des and Selection, 28(10):403-414 (2015).
Decision to grant a European patent received for European U.S. Appl. No. 17/761,159, dated Sep. 10, 2020, 2 pages.
European Search Report and Search Opinion Received for EP Application No. 20191942.0, dated Sep. 16, 2020, 9 pages.
Office Action received for EA Application No. 201990316, dated Dec. 22, 2020, 3 pages (1 page of English Translation and 2 pages of Original Document).
Japanese Office Action for Application No. 2019-508809, dated May 10, 2021, 3 pages.
Arosio et al., On the rale of salt type and concentration on the stability behavior of a monoclonal antibody solution Biophys Chem. Jul. 2012;168-169:19-27.

\* cited by examiner

CONCENTRATION-DEPENDENT SELF-INTERACTION ASSAY

CROSS REFERENCE TO RELATED APPLICATIONS

This application is a national stage application, filed under 35 U.S.C. § 371, of International Patent Application No. PCT/US2017/047630 filed on Aug. 18, 2017, which claims benefit of and priority to U.S. Provisional Application No. 62/376,788 filed on Aug. 18, 2016.

FIELD

The invention relates generally to the selection of therapeutic proteins for development and commercialization; and more specifically to the selection of proteins that have a greater likelihood of readily achieving a high protein concentration with concomitant lower likelihood of forming aggregates. The invention specifically relates to assessing protein colloidal interactions and selecting proteins to formulate at high concentration.

BACKGROUND

Large biological molecules—"biotherapeutics"—are an important class of drugs. Monoclonal antibodies for example offer exquisite therapeutic specificity, long biological half-life, and high safety profiles.

Biotherapeutics given their size and complexity are difficult to manufacture and formulate. Most biotherapeutics are formulated as lyophilized solids or liquid formulations, and stability of these molecules is an important problem. Stability not only impacts shelf life of the final product, but also the manufacturing process.

A large molecule by definition has a large molecular mass. Therefore, a few moles of drug encompass a relatively large mass. For example, an antibody has a molecular mass of about 150,000 grams per mole, whereas a small molecule drug like atorvastatin has a molecular mass of about 560 grams per mole. Therefore, to attain an effective dose, a high mass of protein drug is required. As more drugs are formulated for subcutaneous injection, that large mass has to fit into a small volume. To accommodate therapeutically effective doses, subcutaneous formulations of biotherapeutic drugs must attain high (about 50 mg/mL or more) or very high (about 100-250 mg/mL) concentrations, all while keeping viscosity at a manageable level.

As large molecules are crammed into a small space and the distance between protein molecules decreases, the frequency of colloidal interactions, i.e., the through-space effect of one molecule on another, increases. Protein self-interactions (colloidal interactions) are generally energetically weak, typically reversible and non-specific. The interactions are protein-dependent and are affected by pH, salt and other additives. In some cases the interactions may be net attractive, repulsive, or neutral. The nature and magnitude of the interaction can depend on the concentration of the protein.

Colloidal interactions span a broad spectrum of interactions (potential energy) that are quantified with virial coefficients. $B_{22}$ represents pairwise interactions, $B_{222}$ represents 3-body interactions, $B_{2222}$ represents 4-body interactions, and so on. A positive virial coefficient value represents repulsive interactions, a negative virial coefficient represents attractive interactions, and a zero virial coefficient represents an ideal state.

Colloidal interactions are generally present in protein solutions that exceed ~2 mg/mL and become significant in solutions that exceed ~40 mg/mL. At the lower concentrations, steric and electrostatic forces tend to dominate. The situation becomes more complex with increasing protein concentration. As the concentration of protein increases during production and formulation, colloidal interactions become problematic.

Colloidal interactions impact a variety of downstream processes during protein production. Those forces may be beneficial or detrimental depending on nature and magnitude of the interactions. Colloidal interactions affect chromatographic performance, ultrafiltration and diafiltration (UF/DF), dialysis, viscosity and solution handling, and stability of the protein in solution. Colloidal interactions also impact long term stability during storage, where oligomers and multimers, as well as protein aggregates can form. Assessment of a protein's virial coefficient therefore provides important information before committing resources to the development of a particular protein therapeutic.

Virial coefficient analysis is an established and highly active area of investigation. Current methods of assessing virial coefficient ($B_{22}$, or the closely related $A_2$) for particular proteins include membrane osmometry, sedimentation equilibrium analytical ultra-centrifugation, self-interaction chromatography, static light scattering (SLS), diffusion or sedimentation interaction parameters, and self-interaction nanoparticle spectroscopy (SINS).

For example, Cohen and Benedek (U.S. Pat. No. 4,080, 264A, published Mar. 3, 1978) describe a quasi-elastic light scattering spectroscopic method to measure antigen or antibody aggregation. Publicover and Vincze (U.S. Pat. No. 7,514,938B2, published Apr. 7, 2009) describe the use of dielectric relaxation spectroscopy (DRS) to probe the interaction and aggregation of micron and sub-micron scale particles coated with protein, including antibodies. Holman et al., (US20070291265A1, published Dec. 20, 2007) describe a bifurcated fiber optic system for measuring light scattering and concentration signals to measure aggregation of macromolecules. Obrezanova et al. (mAbs, 7(2): 352-363, 2015) describe the use of size exclusion high pressure liquid chromatography (SE-HPLC) and an oligomer detection assay, which is an optical density microtiter plate antibody capture assay, to systematically measure the aggregation propensity of over 500 antibodies. Geoghegan et al. (mAbs, 8(5): 941-950, 2016) describe the use of hydrophobic interaction chromatography (HIC) retention time, affinity-capture SINS, and dynamic light scattering to measure monoclonal antibody self-interaction, viscosity and stability. An overview of the current methods used to assess colloidal protein interactions is provided by Geng, et al. (J Pharm Sci., 103(11): 3356-3363, 2014).

Self-interaction nanoparticle spectroscopy (SINS) for the assessment of monoclonal antibody self-association is described by Sule at al., (Biophys. J., 101: 1749-1757, 2011). Briefly, antibodies are adsorbed onto gold nanoparticles, which are then combined with a buffer in 96-well microtiter plates. As the nanoparticles aggregate due to the self-association of the adherent antibodies, the absorbance spectrum of the nanoparticles changes. This change in surface plasmon resonance correlates with particle association. The assay provides a binary readout of "self-association" or "no self-association" based on whether the absorbance peak shifts or changes in amplitude. Sule et al. (Mol. Pharmaceutics, 10: 1322-1331, 2013) describe an improved SINS method called affinity-capture self-interaction nanoparticle spectroscopy (AC-SINS). Here, human polyclonal antibodies are first fixed to the nanoparticles, then the coated particles are contacted with low concentration/low purity antibody samples, which are then captured by the anti-human coating. AC-SINS enables the rapid screening of cell supernatants without the need for extensive antibody purification. AC-SINS, like SINS, provides a binary assessment of positive self-association or no self-association of the subject antibodies.

Proteins are complex molecules and often show unpredictable behavior under varying conditions. The state-of-the art provides some means for observing protein self-association, but does not provide a rapid and accurate means to determine the propensity of a protein to undergo self-association under myriad different conditions. Some proteins are stable under some conditions, but unstable under other conditions. There remains a need in the art for an assay to determine the dynamic range of a protein's attractiveness and repulsiveness under changing conditions.

SUMMARY

The inventors developed a method for determining the potential of a protein to self-assemble (i.e., the protein's inherent repulsiveness or attractiveness) across a dynamic range of conditions. Consequently the method may be understood as a method for determining the stability of self-associated proteins or a method for determining the stability of aggregated proteins. As is further elaborated herein, the protein may be a single type of protein or a combination of any proteins of different origins. The method, called concentration-dependent self-interaction nanoparticle spectroscopy (CD-SINS) measures the propensity of a protein to self-assemble under changing concentration and various ionic strength and pH conditions. The method enables the prediction of the protein at high or very high concentration conditions and informs the selection of proteins for commercial development. The method also provides for information on how to formulate a pharmaceutical composition comprising high concentrations of one or more biopharmaceutical drugs whilst maintaining long shelf life without association of the biopharmaceutical drug or drugs. The method also enables for information on how to formulate a composition fulfilling required specifications on physical properties such as e.g. a suitable rheology/viscosity to allow for a specific desired route of administration. The invention also allows for a more rapid screening of biopharmaceuticals using less amount of material to arrive at a suitable formulation or selecting suitable candidates for further drug development.

In a first aspect, the invention provides bioanalytical mixture comprising a plurality of nanoparticles, a protein, and a buffered salt. The protein exists in at least two phases in the mixture: an adherent phase, and a soluble phase. The adherent phase includes proteins that are adhered to (i.e., coating) the nanoparticles. The soluble phase includes proteins that are dissolved in the buffered salt solution. In some embodiments, the protein exists in a third phase, where the proteins are self-associated as dimer, trimers, tetramers, or higher order multimers, including aggregated coated nanoparticles.

In one embodiment, the nanoparticle is a gold nanoparticle. In some embodiments, the nanoparticle has a diameter of about 20 nm to about 100 nm. In a particular embodiment, the nanoparticle is a gold nanoparticle having a diameter of about 20 nm.

In one embodiment, each nanoparticle is coated with protein. In some embodiments, most or all of the nanoparticle surfaces are saturated with protein, meaning that the surface is completely occupied by protein and no bare surface remains for a protein to adhere. In some embodiments, most or all of the nanoparticle surfaces are saturated with protein prior to adding other components to the mixture, such as a suitable salt or a buffered salt.

In one embodiment, the mixture contains about $6 \times 10^{11}$ to about $7 \times 10^{11}$ nanoparticles per milliliter of mixture. In a particular embodiment, the mixture contains about $6.3 \times 10^{11}$ nanoparticles per mL. While not wishing to be bound by theory and assuming that an average protein can be modeled as a 10 nm sphere, the theoretical upper limit for the number of 10 nm spheres needed to coat a 20 nm sphere is about 30. Approximately 15 to 20 antibody molecules can be estimated to bind a single 20 nm nanoparticle. Therefore, ~2.5 µg/mL of an antibody is estimated to be the minimum concentration necessary to completely cover $6.3 \times 10^{11}$ nanoparticles (20 nm)/mL. In some embodiments, the mixture comprises about 2 µg/mL to about 512 µg/mL of protein.

In some embodiments, the protein included in the mixture is a therapeutic antibody. In some embodiments, the protein comprises an immunoglobulin Fc domain. In some embodiments, the protein is an antigen-binding protein. Antigen-binding proteins include antibodies, antibody fragments, antibody derivative, Fc-fusion proteins and receptor -Fc-fusion proteins. In one embodiment, the protein is a monoclonal antibody. In a more specific embodiment, the monoclonal antibody is a human or humanized antibody. In some embodiments, the monoclonal antibody may be a monospecific antibody or a bispecific antibody.

In some embodiments, the buffered salt comprises a buffer and a salt. In some embodiments, the buffer provides ionic strength. In some embodiments, the salt buffers the mixture. The salt may in principle be any suitable salt known in the art and may be e.g. any chloride, bromide, phosphate, sulfate or ammonium salt, or any combinations thereof. Non-limiting examples are e.g. sodium chloride, potassium chloride, potassium phosphate, ammonium chloride etc. In one embodiment, the salt comprises sodium chloride. The salt (e.g., sodium chloride) may be present at a concentration of about 2 mM to about 300 mM. In particular embodiments, the salt is present in the mixture at a concentration of about 2 mM, about 20 mM, or about 200 mM.

In one embodiment, the buffer comprises 2-(N-morpholino)ethanesulfonic acid (MES). In a specific embodiment, the MES is present in the mixture at a concentration of about 10 mM and a pH of about 6.

In a second aspect, the invention provides a method for determining the potential of a protein to self-associate. In one embodiment, the method comprises the steps of combining a protein, a plurality of nanoparticles, and a buffered salt to form a sample; exciting the sample with light; measuring the light transmitted through the sample; and calculating the first absorbance intensity ratio of the sample. The process is repeated at least one more time, each time changing one or more parameters, and obtaining a second, third, etc. absorbance ratio. The multiple absorbance intensity ratios obtained from a given protein may be plotted for analysis. Those parameters include salt type (i.e., neutral, chaotropic, kosmotropic), salt concentration, pH, protein concentration, the inclusion or exclusion of additional ingredients. When the absorbance intensity ratio exceeds a threshold value, the protein is considered to be favorable for dispensing at high concentration. A protein considered to be favorable for dispensing at high concentration is expected to remain stable at a high concentration and to be less prone to aggregation.

In some embodiments, the protein is a therapeutic antibody. In some embodiments, the protein comprises an immunoglobulin Fc domain. In some embodiments, the protein is an antigen-binding protein. Antigen-binding proteins include antibodies, antibody fragments, antibody derivative, Fc-fusion proteins and receptor -Fc-fusion proteins. In one embodiment, the protein is a monoclonal antibody. In a more specific embodiment, the monoclonal antibody is a human or humanized antibody. In some embodiments, the monoclonal antibody may be a monospecific antibody or a bispecific antibody.

In some embodiments, the protein is added to the sample to a final concentration of about 2 μg/mL to about 512 μg/mL.

In some embodiments, the nanoparticle is a gold nanoparticle. In some embodiments, the gold nanoparticle has a diameter of about 20 nm to about 100 nm. In one embodiment, the diameter of the gold nanoparticle is about 20 nm.

In some embodiments, the nanoparticles are added to the sample to a final concentration of about $5 \times 10^{11}$ to about $8 \times 10^{11}$ nanoparticles per mL, about $6 \times 10^{11}$ to about $6.5 \times 10^{11}$ nanoparticles per mL, or about $6.3 \times 10^{11}$ nanoparticles per mL.

The buffered salt may contain a buffer, a buffer that confers ionic strength, a salt, a salt that has buffering capacity, or a salt and a buffer. In one embodiment, the salt comprises sodium chloride. The salt (e.g., sodium chloride) may be present at a concentration of about 2 mM to about 300 mM. In some specific embodiments, the salt is present in the mixture at a concentration of about 2 mM, about 5 mM, about 10 mM, about 20 mM, about 50 mM, about 75 mM, about 100 mM, about 110 mM, about 120 mM, about 150 mM, about 175 mM, about 200 mM, or about 300 mM.

In one embodiment, the buffer comprises 2-(N-morpholino)ethanesulfonic acid (MES). In a specific embodiment, the MES is present in the mixture at a concentration of about 10 mM and a pH of about 6.

In some embodiments, the excitation light is white light comprising wavelengths spanning the visible spectrum. In some embodiments, the transmitted light is measured at multiple wavelengths ranging from about 450 nm to about 750 nm.

The absorbance intensity ratio is a measure of the relative intensity of light absorbance relative to a standard or control. The control may by external or internal. In one embodiment, the absorbance intensity ratio is calculated by dividing the maximum intensity (optical density or absorbance) of the peak absorbance wavelength of the sample by the initial absorbance intensity observed. In one embodiment, the initial observed absorbance intensity is the absorbance intensity observed at 450 nm. In that embodiment, the absorbance intensity ratio is peak absorbance ($A_{peak}$)/absorbance at 450 nm ($A_{450}$ or $A_{init}$). In that embodiment, the threshold value of the absorbance intensity ratio is about 1.5 to about 2. In a specific embodiment, the threshold value of the absorbance intensity ratio is about 1.7.

In one embodiment, a protein considered favorable for dispensing at high concentration is combined with an excipient to form a formulated drug substance (FDS) or drug product (DP). In one embodiment, the protein is formulated to a final concentration of about 50 mg/mL to about 250 mg/mL.

In one embodiment the excipient includes a tonicifier, a buffer, a surfactant, a stabilizer, or any combination of two or more thereof. In one embodiment, the tonicifier is a salt. In a specific embodiment, the salt is sodium chloride. In one embodiment, the buffer buffers at about pH 6 to about pH 7.

In a specific embodiment, the buffer is histidine. In another specific embodiment, the buffer is phosphate. In one embodiment, the surfactant is a polysorbate, such as polysorbate 20 or polysorbate 80. In one embodiment, the stabilizer is a sugar, such as sucrose or trehalose. In another embodiment, the stabilizer is an amino acid, such as proline or arginine.

In a third aspect, the invention provides a method of manufacturing a therapeutic protein. In one embodiment, the method comprises the step of selecting a protein having high colloidal stability from a plurality of different proteins of varying unknown colloidal stability; producing the selected protein in a host cell; purifying the protein; and combining the protein at a high concentration with an excipient to form a formulated drug substance or drug product where the protein is stable. In one embodiment, less than 10% of the protein in the formulated drug substance or drug product is aggregated.

In one embodiment, the step of selecting the protein having high colloidal stability comprises the steps of combining the protein with a nanoparticle and a buffered salt to form a sample; exciting the sample with light; measuring the light transmitted by the sample; and calculating the absorbance intensity ratio of the sample. This selecting step is repeated one or more times with one or more parameters being changed. The parameters that are changed include salt type, salt concentration, pH, protein concentration, and the inclusion or exclusion of additional ingredients. When the absorbance intensity ratio exceeds a threshold value the protein is selected as having high colloidal stability.

In some embodiments, the excitation light is white light comprising wavelengths spanning the visible spectrum. In some embodiments, the transmitted light is measured at multiple wavelengths ranging from about 450 nm to about 750 nm.

The absorbance intensity ratio is a measure of the relative intensity of light absorbance relative to a standard or control. The control may by external or internal. In some embodiments, the absorbance intensity ratio is calculated by dividing the maximum intensity (optical density or absorbance) of the peak absorbance wavelength of the sample by (1) the initial absorbance intensity observed in that sample (internal), or by (2) the initial absorbance intensity observed in a sample of nanoparticles the absence of protein (external). In one embodiment, the initial observed absorbance intensity is the absorbance intensity observed at 450 nm. In that embodiment, the absorbance intensity ratio is peak absorbance ($A_{peak}$)/absorbance at 450 nm ($A_{450}$ or $A_{init}$). In that embodiment, the threshold value of the absorbance intensity ratio is about 1.5 to about 2. In a specific embodiment, the threshold value of the absorbance intensity ratio is about 1.7.

In a further embodiment, the invention relates to a composition comprising a biotherapeutic drug (such as e.g. a protein or antibody) in a high concentration. Specifically, the composition may be such that no more than about 10% of the total protein species is present as an irreversible aggregate at the concentration of the biotherapeutic drug. Alternatively, the composition is such that the threshold value as discussed herein is e.g. in range of e.g. about 1.5 to about 2.0 ($A_{peak}/A_{450}$). A further alternative is where the threshold value is e.g. about 1.5, about 1.6, about 1.7, about 1.8, about 1.9, or about 2.0 ($A_{peak}/A_{450}$). In some embodiments, the threshold value is in range of about 0.7 to about 1.0 ($A_{peak}/A_{control}$). A further alternative is where the threshold value is e.g. about 0.7, about 0.8, about 0.9, or about 1.0 ($A_{peak}/A_{control}$). In yet a further embodiment, the composition is such that no more than about 10% of the total protein species is present as an irreversible aggregate at the concentration of the biotherapeutic drug and such that the composition has a threshold value as discussed herein is e.g. in range of e.g. about 1.5 to about 2.0 ($A_{peak}/A_{450}$) or where the threshold value is e.g. about 1.5, about 1.6, about 1.7, about 1.8, about 1.9, or about 2.0 ($A_{peak}/A_{450}$), and/or where the threshold value is in range of about 0.7 to about 1.0 ($A_{peak}/A_{control}$), or where the threshold value is e.g. about 0.7, about 0.8, about 0.9, or about 1.0 ($A_{peak}/A_{control}$). The concentration of the biopharmaceutical drug may be about 50 mg/mL or more. Alternatively, the concentration of the biopharmaceutical drug may be in range of e.g. about 50 mg/mL to about 500 mg/mL, such as e.g. about 50 mg/mL to about 250 mg/mL, such as e.g. about 100 mg/mL to about 250 mg/mL.

In one embodiment the invention relates to a composition obtainable by the method for determining the potential of a protein to self-assemble as disclosed herein.

In yet a further aspect, the invention relates to a composition comprising a biotherapeutic drug (such as e.g. a protein or antibody) in a high concentration for use in medicine. Depending on the drug, a person skilled in the art will know which or what clinical conditions that may be treated by administering the composition to a subject in need thereof. The composition may be such that no more than about 10% of the total protein species is present as an irreversible aggregate at the concentration of the biotherapeutic drug. Alternatively, the composition is such that the threshold value as discussed herein is e.g. in range of e.g. about 1.5 to about 2.0 ($A_{peak}/A_{450}$). A further alternative is where the threshold value is e.g. about 1.5, about 1.6, about 1.7, about 1.8, about 1.9, or about 2.0 ($A_{peak}/A_{450}$). In some embodiments, the threshold value is in range of about 0.7 to about 1.0 ($A_{peak}/A_{control}$). A further alternative is where the threshold value is e.g. about 0.7, about 0.8, about 0.9, or about 1.0 ($A_{peak}/A_{control}$). In yet a further embodiment, the composition is such that no more than about 10% of the total protein species is present as an irreversible aggregate at the concentration of the biotherapeutic drug and such that the composition has a threshold value as discussed herein is e.g. in range of e.g. about 1.5 to about 2.0 ($A_{peak}/A_{450}$) or where the threshold value is e.g. about 1.5, about 1.6, about 1.7, about 1.8, about 1.9, or about 2.0 ($A_{peak}/A_{450}$), and/or where the threshold value is in range of about 0.7 to about 1.0 ($A_{peak}/A_{control}$), or where the threshold value is e.g. about 0.7, about 0.8, about 0.9, or about 1.0 ($A_{peak}/A_{control}$). The concentration of the biopharmaceutical drug may be about 50 mg/mL or more. Alternatively, the concentration of the biopharmaceutical drug may be in range of e.g. about 50 mg/mL to about 500 mg/mL, such as e.g. about 50 mg/mL to about 250 mg/mL, such as e.g. about 100 mg/mL to about 250 mg/mL. The composition may be administered as a single dose or multiple doses as considered needed for obtaining desired result in treatment. Alternatively, the invention relates to a composition comprising a biotherapeutic drug (such as e.g. a protein or antibody) in a high concentration for manufacture of a medicament in the treatment of a disease or diseases treatable or curable by said biotherapeutic drug.

In one embodiment, the invention provides a method of preparing a biopharmaceutical composition (such as e.g. a protein or an antibody) such that the resulting composition possesses a suitable rheology. Specifically, the method for determining the potential of a protein to self-assemble as disclosed herein allows for determination of an array of provision of a stable composition comprising a high biopharmaceutical drug concentration. One important attribute of such composition is the viscosity. Consequently, the method of the invention will allow for the preparation of a composition with desired physical properties such that the composition may be administered via a desired route or mode of administration. One exemplary administration route may be administration by injection. In such instance, it is thus important to have a viscosity of the prepared composition enabling injection by e.g. a syringe and cannula. Such cannula may be a cannula of size such as e.g. 6 G, 8 G, 9 G, 10 G, 11 G 12 G, 13 G, 14 G, 16 G, 19 G, 20 G, 21 G, 22 G, 23 G, 24 G, or 26 G. The term "viscosity" refers to the dynamic or absolute viscosity (at 20° C. and normal pressure) which is a measure of the resistance of a fluid which is being deformed by either shear stress or extensional stress. "Viscosity" thus describes a fluid's internal resistance to flow and may be thought of as a measure of fluid friction. Consequently, the less viscous something is, the greater its ease of movement (fluidity). In the present context, the relevant ranges of viscosity are from about 10-10.000 mPa·s, such as e.g. about 20-9000 mPa·s, such as e.g. about 30-8000 mPa·s, such as e.g. about 40-7000 mPa·s, such as e.g. about 50-6000 mPa·s, such as e.g. about 70-5000 mPa·s, such as e.g. about 90-4000 mPa·s, such as e.g. about 100-3000 mPa·s or about 10 mPa·s, or about 20 mPa·s, or about 30 mPa·s, or about 40 mPa·s, or about 50 mPa·s or alternatively from about 1 mPa·s to about 20 mPa·s, such as about 2 mPa·s, such as about 3 mPa·s, such as about 4 mPa·s, such as about 5 mPa·s such as about 6 mPa·s, such as about 7 mPa·s such as about 10 mPa·s, about 13 mPa·s, about 15 mP·s, such as e.g. about 20 mPa·s.

Other units for measurement of viscosity are well-known, for example, 1 centipoise is equivalent to 1 mPa·s. Without being bound to any particular theory, a typical protein at a low concentration (i.e. less than or equal to 10 mg/mL) exhibits a viscosity of about 10 cP. As such, a highly concentrated protein composition, e.g. an antibody composition, exhibiting a viscosity below about 10 centipoise (below about 10 mPa·s) is highly suitable for use as a biopharmaceutical composition. A protein composition (at a high concentration) having a viscosity from about 10 to about 15 centipoise (about 10 mPa·s to about 15 mPa·s) is safe to proceed with in the manufacturing and drug development process. A protein composition (at a high concentration) having a viscosity from about 15 to about 20 centipoise (about 15 mPa·s to about 20 mPa·s) informs to proceed with caution in the manufacturing and drug development process. A protein composition (at a high concentration) having a viscosity greater than about 20 centipoise (greater than about 20 mPa·s) informs of problematic manufacturing and drug development processing. The viscosity may be manipulated by the various components and ingredients as disclosed herein. "Soluble" and "highly soluble" also refer to a protein having a suitable viscosity for any of the uses disclosed herein, e.g. for making and using a biopharmaceutical composition.

In one embodiment, the protein is an antigen-binding protein, for example an antibody, an antibody fragment or a receptor-Fc-fusion protein.

In one embodiment, the host cell in which the protein is made is a Chinese hamster ovary (CHO) cell or a derivative of a CHO cell, such as a CHO-K1 cell or an EESYR® cell (see Chen et al., US771997B2, published Aug. 10, 2010).

In one embodiment, the step of purifying the protein comprises subjecting the protein to (1) one or more step of affinity chromatography, ion exchange chromatography, hydrophobic interaction chromatography, mixed mode chromatography, and hydroxyapatite chromatography; and (2) one of both of ultrafiltration and diafiltration.

In one embodiment, the protein is formulated at a final concentration that is at least 50 mg/mL. In one embodiment, the concentration of the protein is about 50 mg/mL to about 250 mg/mL.

In one embodiment the excipient with which the protein is combined to form the formulated drug substance or drug product comprises one or more of a tonicifier, a buffer, a surfactant, and stabilizer. In one embodiment, the tonicifier is a salt. In a specific embodiment, the salt is sodium chloride. In one embodiment, the buffer buffers at about pH 6 to about pH 7. In a specific embodiment, the buffer is histidine. In another specific embodiment, the buffer is phosphate. In one embodiment, the surfactant is a polysorbate, such as polysorbate 20 or polysorbate 80. In one embodiment, the stabilizer is a sugar, such as sucrose or trehalose. In another embodiment, the stabilizer is an amino acid, such as proline or arginine.

DRAWINGS

FIG. 1 depicts an absorbance profile of dispersed 20 nm gold nanoparticles (line A) and agglomerated 20 nm gold nanoparticles (line B). The Y-axis depicts optical density in arbitrary absorbance units. The X-axis depicts transmitted light wavelength in nanometers (nm).

FIG. 2 depicts a scatter plot of absorbance intensity ratios of different concentrations of monoclonal antibody 2 (mAb2) and 20 nm gold nanoparticles in 2 mM salt (circles), 20 mM salt (squares) and 200 mM salt (triangles). The Y-axis depicts the ratio of peak absorbance intensity of each sample condition over the initial absorbance intensity. The X-axis depicts the concentration of mAb2 in micrograms per milliliter.

FIG. 3 depicts a scatter plot of absorbance intensity ratios of different concentrations of monoclonal antibody (mAb) 1 (open symbols) and mAb5 (closed symbols) in the presence of 20 nm gold nanoparticles in 2 mM salt (squares), 20 mM salt (triangles) and 200 mM salt (circles). The Y-axis depicts the ratio of peak absorbance intensity of each sample condition over the initial absorbance intensity. The X-axis depicts the concentration of mAb1 in micrograms per milliliter. The boxed area to the left (A) represents conditions of higher colloidal repulsive conditions having high selection value, the boxed area in the middle (B) represents conditions of mixed repulsive and attractive conditions having cautious or mixed selection value, and the boxed area to the right (C) represents conditions of attractiveness having problematic or low selection value.

FIG. 4 depicts an overlay of multiple absorbance profiles of dispersed 20 nm gold nanoparticles combined with human serum albumin (HSA) of varying concentration (3.125 µg/mL, 6.25 µg/mL, 12.5 µg/mL, 25 µg/mL, 50 µg/mL, 100 µg/mL, 200 µg/mL and 400 µg/mL in order from top to bottom at right-most [750 nm] portion of curve). The Y-axis depicts arbitrary absorbance in arbitrary units. The X-axis depicts transmitted light wavelength in nanometers (nm).

FIG. 5 depicts a scatter plot of absorbance intensity ratios of different concentrations of HSA derived from the raw absorbance spectra depicted in FIG. 4 and 20 nm gold nanoparticles in 2 mM salt (circles), 20 mM salt (squares) and 200 mM salt (triangles). The Y-axis depicts the ratio of peak absorbance intensity of each sample condition over the initial absorbance intensity. The X-axis depicts the concentration of HSA in micrograms per milliliter.

FIG. 6 depicts a scatter plot of absorbance intensity ratios of different concentrations of monoclonal antibody 1 (mAb1) and 20 nm gold nanoparticles in 2 mM salt (circles), 20 mM salt (squares) and 200 mM salt (triangles). The Y-axis depicts the ratio of peak absorbance intensity of each sample condition over the initial absorbance intensity. The X-axis depicts the concentration of mAb1 in micrograms per milliliter.

FIG. 7 depicts a scatter plot of scattered light intensity of solutions of mAb1 at different concentrations and ionic salt concentrations: 2 mM NaCl (circles), 20 mM NaCl (squares), and 200 mM NaCl (triangles). The Y-axis represents light scattering intensity in arbitrary absorbance units. The X-axis represents concentration of mAb1 in grams per liter. The solid line represents an ideal hard sphere of comparable diameter.

FIG. 8 depicts a scatter plot of absorbance intensity ratios of different concentrations of monoclonal antibody 6 (mAb6) and 20 nm gold nanoparticles in 2 mM salt (circles), 20 mM salt (squares) and 200 mM salt (triangles). The Y-axis depicts the ratio of peak absorbance intensity of each sample condition over the initial absorbance intensity. The X-axis depicts the concentration of mAb6 in micrograms per milliliter.

FIG. 9 depicts a scatter plot of scattered light intensity of solutions of mAb6 at different concentrations and ionic salt concentrations: 2 mM NaCl (circles), 20 mM NaCl (squares), and 200 mM NaCl (triangles). The Y-axis represents light scattering intensity in arbitrary absorbance units. The X-axis represents concentration of mAb6 in grams per liter. The solid line represents an ideal hard sphere of comparable diameter.

FIG. 10 depicts a scatter plot of absorbance intensity ratios of different concentrations of monoclonal antibody 3 (mAb3) and 20 nm gold nanoparticles in 2 mM salt (circles), 20 mM salt (squares) and 200 mM salt (triangles). The Y-axis depicts the ratio of peak absorbance intensity of each sample condition over the initial absorbance intensity. The X-axis depicts the concentration of mAb3 in micrograms per milliliter.

FIG. 11 depicts a scatter plot of absorbance intensity ratios of different concentrations of monoclonal antibody 4 (mAb4) and 20 nm gold nanoparticles in 2 mM salt (circles), 20 mM salt (squares) and 200 mM salt (triangles). The Y-axis depicts the ratio of peak absorbance intensity of each sample condition over the initial absorbance intensity. The X-axis depicts the concentration of mAb4 in micrograms per milliliter.

FIG. 12 depicts a scatter plot of absorbance intensity ratios of different concentrations of monoclonal antibody 5 (mAb5) and 20 nm gold nanoparticles in 2 mM salt (circles), 20 mM salt (squares) and 200 mM salt (triangles). The Y-axis depicts the ratio of peak absorbance intensity of each sample condition over the initial absorbance intensity. The X-axis depicts the concentration of mAb5 in micrograms per milliliter.

Figure 15:
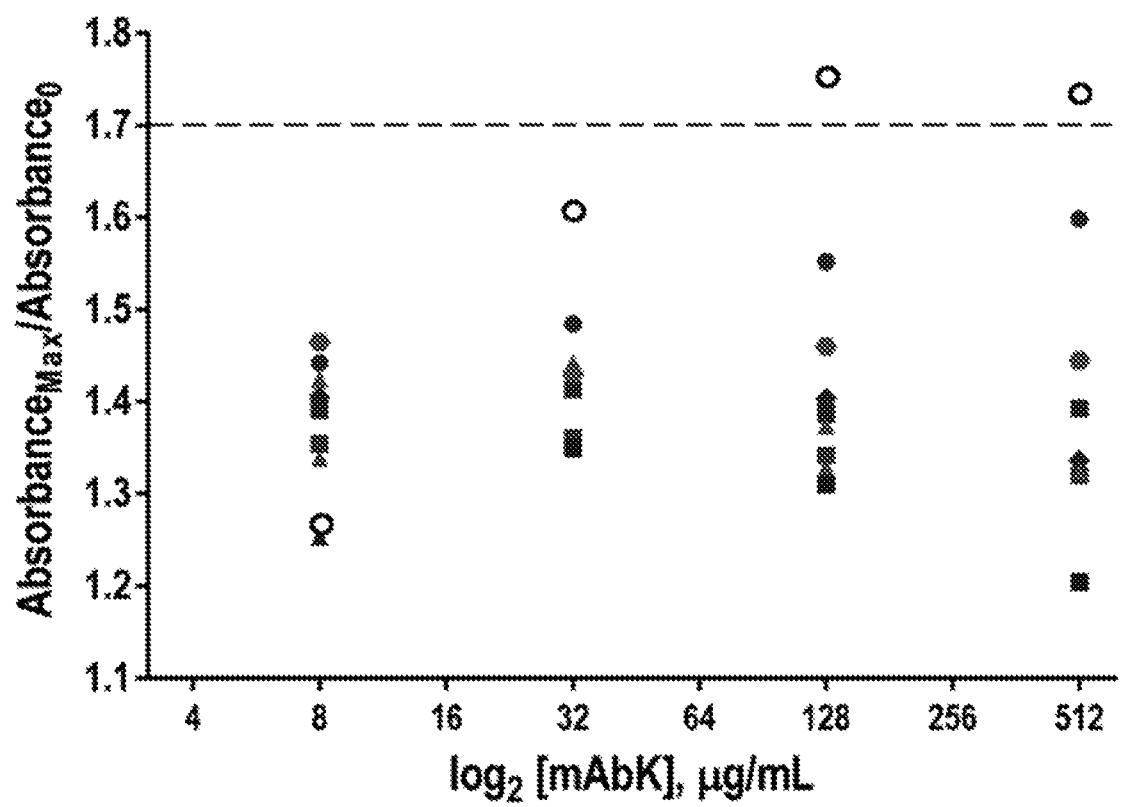

FIG. 15 depicts a CD-SINS scatter plot of absorbance intensity ratios of different concentrations of monoclonal antibody 7 (mAb7) (8 μg/mL, 32 μg/mL, 128 μg/mL, and 512 μg/mL mAbK) combined with different benzoate compounds. When combined with p-aminobenzoic acid [PABA (-○-), open circle], mAb7 exhibited a favorable dynamic colloidal interaction profile in which the absorbance intensity ration (Y-axis) exceeds 1.6.

Figure 16:
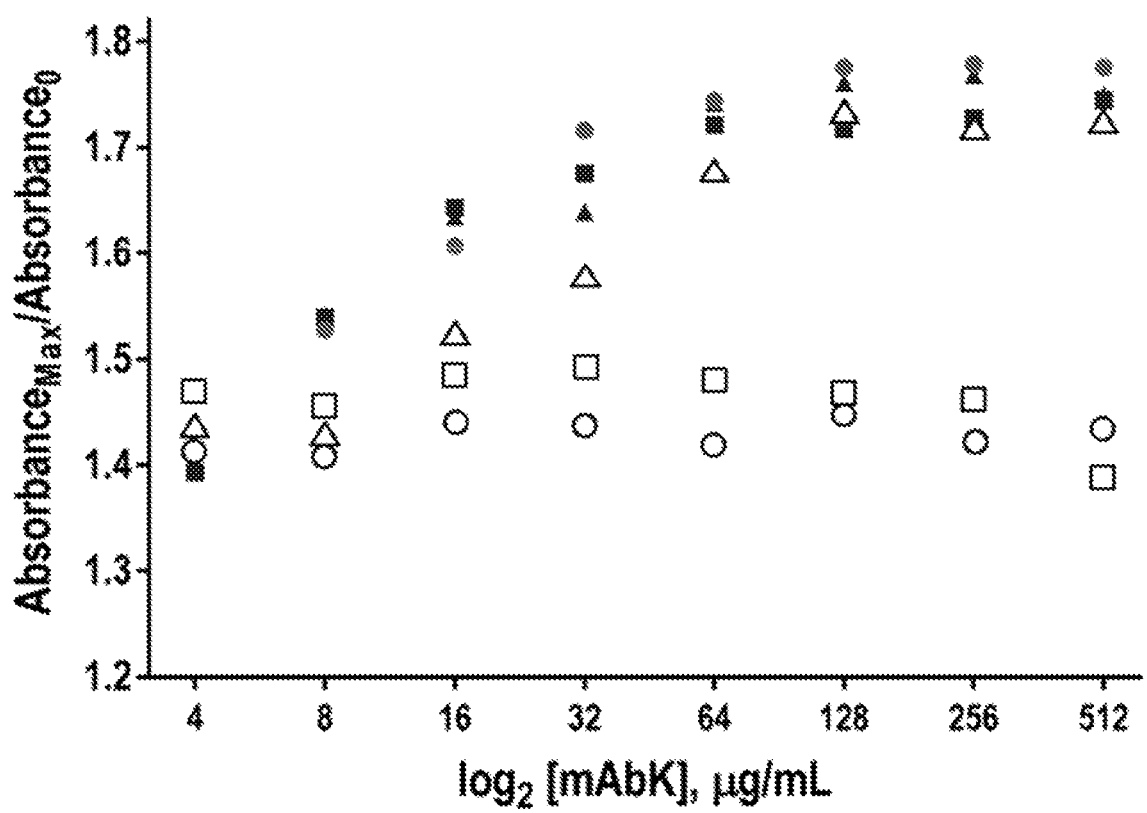

FIG. 16 depicts a CD-SINS scatter plot of absorbance intensity ratios of different concentrations of monoclonal antibody K (mAbK) in the presence of varying concentrations of p-aminobenzoic acid (PABA). The X-axis depicts log 2 of the concentration of mAb7 in micrograms per milliliter. The Y-axis depicts the absorbance intensity ratio. Open circles (-○-) represent no PABA, open squares (-□-) represent 12 mM PABA, open triangles (-△-) represent 18 mM PABA, closed circles (-•-) represent 24 mM PABA, closed squares (-■-) represent 30 mM PABA, and closed triangles (-▲-) represent 36 mM PABA.

Figure 17:
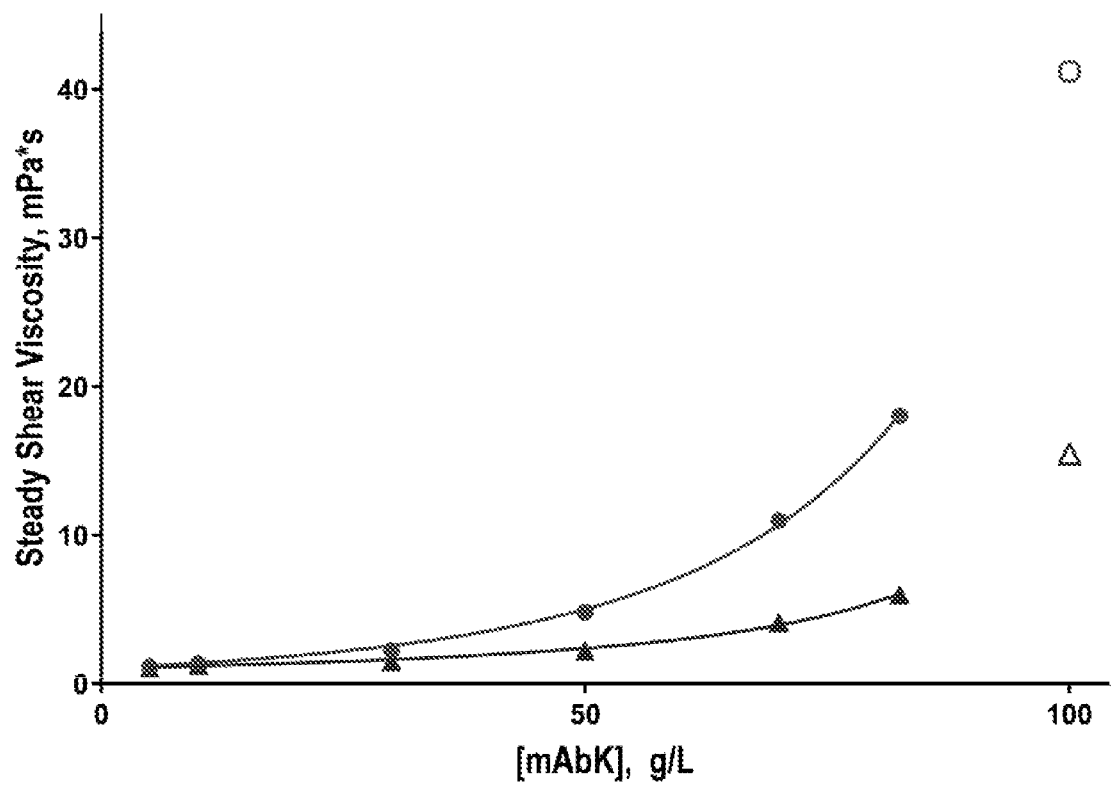

FIG. 17 depicts a dot plot of the steady shear viscosity (in mPa*s) of a mAb7 solution containing no PABA (closed circles [-•-]) or 20 mM PABA (closed triangles [-▲-]) as a function of mAb7 concentration in g/L. Open symbols represent extrapolated viscosity of solutions expected to contain 100 g/L mAb7.

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about", when used in reference to a particular recited numerical value, means that the value may vary from the recited value by no more than 15%. For example, as used herein, the expression "about 100" includes 85 and 115 and all integer and non-integer values in between (e.g., 86, 86.001, 87, 88, 88.3, 89, etc. . . . ).

Absolute amounts and relative amounts of excipients, ingredients, and other materials may be described by mass, or moles. Units of mass may be expressed as grams, milligrams, micrograms, and the like). The term "weight" as in "weight/volume" or "w/v" means "mass". Relative amounts may be expressed as percent weight (i.e., percent mass), wherein one (1) percent weight to volume (w/v) means 1 gram of material per 100 milliliter of volume. Also for example, one (1) part ingredient "A" per one (1) part ingredient "B" by weight means e.g. that for every one (1) gram of ingredient "A" there is one (1) gram of ingredient "B". Also for example, one percent (1%) by weight of ingredient "A" means e.g. that for every 100 grams of total mass of a particle there is one (1) gram of ingredient "A". Relative amounts of an ingredient may also be expressed in terms of moles or number of molecules per given volume, e.g., millimoles per liter (millimolar (mM)), or per other ingredient, e.g., X part ingredient "A" per Y part ingredient "B" by mole means for every X moles of "A" there are Y moles of "B"

Although any methods and materials similar or equivalent to those described herein can be used in the practice or testing of the present invention, the exemplar methods and materials are now described. All publications mentioned herein are incorporated herein by reference in their entirety. Assay to Determine Dynamic Colloidal Stability: Concentration-Dependent Self-Interaction Nanoparticle Spectroscopy (CD-SINS)

An improvised SINS-based assay for determining the dynamic virial range for proteins is provided. A protein exhibits complex behavior, which is very sensitive to the chemical physical environment of the protein. Therefore, assessing the virial coefficient of a protein under a particular set of environmental circumstances is insufficient to determine the virial coefficient of that protein in other environments. Obtaining multiple virials for a given protein under myriad conditions is painstaking and time consuming. The inventors herein disclose a high through put assay to determine the dynamic colloidal stability of a protein, which informs the selection of a protein that can be formulated or otherwise kept at a high concentration without having problems associated with aggregation, or at least minimizing potential aggregation problems.

Figure 1:
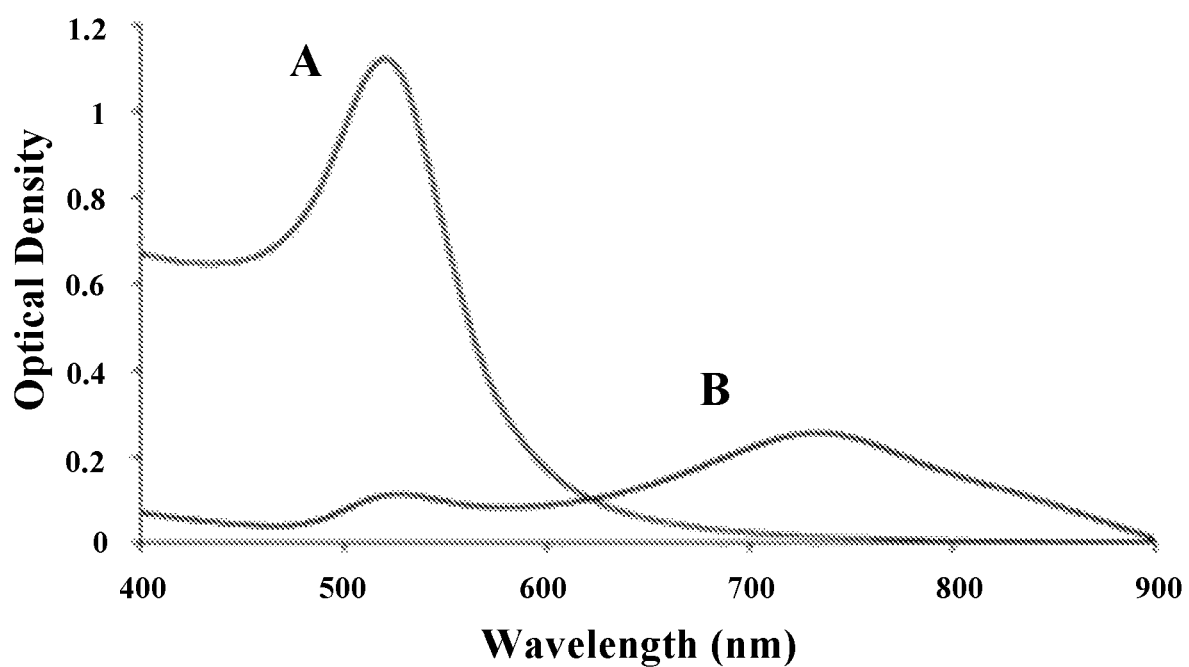

That assay employs SINS in a novel way by assessing nanoparticle aggregation under conditions of varying protein concentration, varying ionic strength, varying pH, and other conditions. As described above and in Sules (2011), gold nanoparticles are coated with protein and placed into buffered solution. As the nanoparticles aggregate due to protein self-association, the surface plasmon resonance of the particles changes: the maximum absorbance shifts to the higher wavelength (red shift); and the absorbance is of a lower intensity, i.e., the absorbance profile spreads out and moves left (FIG. 1). Here, the uncoated 20 nm gold nanoparticles have a peak absorbance at about 520 to 530 nm.

A comparison of conventional SINS with the well-established static light scattering (SLS) method of determining $B_{22}$ or $A_2$ shows general agreement for most antibodies that were tested. Table 1 compares the peak absorbance of beads coated with specific different monoclonal antibodies and human serum albumin (HSA) under the SINS assay to the $A_2$ virials for the same proteins determined by SLS. As shown in Table 1, SINS analysis readily distinguishes attractive (negative $A_2$) from repulsive (positive $A_2$) systems. However, the conventional SINS and SLS assays show no dynamic range for repulsive conditions. Also, the few discrepancies between conventional SINS and SLS indicate complex behavior of some proteins.

TABLE 1

| Protein | Nature of system | 2 mM NaCl | | 20 mM NaCl | | 200 mM NaCl | |
|---|---|---|---|---|---|---|---|
| | | SINS | $A_2$ | SINS | $A_2$ | SINS | $A_2$ |
| HSA | Repulsive | 526 | 1.17E-4 | 526 | 9.68E-5 | 528 | 7.85E-5* |
| mAb1 | Repulsive | 530 | 1.72E-4 | 531 | 6.70E-5 | 532 | 1.34E-5 |
| mAb2 | Mixed | 583 | -2.36E-5 | 536 | -1.44E-5 | 534 | 1.47E-5 |

TABLE 1-continued

| Protein | Nature of system | 2 mM NaCl | | 20 mM NaCl | | 200 mM NaCl | |
| --- | --- | --- | --- | --- | --- | --- | --- |
| | | SINS | $A_2$ | SINS | $A_2$ | SINS | $A_2$ |
| mAb3 | Attractive | 556 | −3.39E−5 | 555 | −4.68E−5 | 565 | NP |
| mAb4 | Repulsive | 531 | −5.90E−5 | 533 | −1.06E−5 | 535 | 1.38E−5 |
| mAb5 | Mixed | 562 | −1.09E−5 | 535 | −2.14E−5 | 530 | −7.67E−6 |

The inventors observed that some proteins are capable of being stable at high concentrations, but show negative A2 or red-shifted maximum absorbance spectra ($\lambda_{max}$). for example, mAb5 can readily attain a concentration of about ~200 g/L and remain stable, yet its $A_2$ is negative and its $\lambda_{max}$ is red-shifted at the lower ionic strength. Similarly, mAb2 can readily attain a concentration of about ~175 g/L and remain stable, yet its $A_2$ is negative at lower salt concentration and its $\lambda_{max}$ is red-shifted at the lower ionic strength.

Here, an improved method of SINS is disclosed. The method provides dynamic colloidal stability data for proteins in order to assess protein-specific phenomena earlier in the development timeline, while circumventing the need for large quantities of protein. The method employs coated nanoparticle surface plasmon resonance in the presence of varying amounts of protein in solution in excess of the amounts required to coat the nanoparticles. Absorbance profiles are observed, absorbance intensity ratios calculated for each variant sample, and plotted to determine the dynamic colloidal stability determined.

In one embodiment, for each sample in a plurality of samples used to determine multiple individual absorbance intensity ratio values for a given subject protein, nanoparticles are combined with varying amounts of protein in excess of the minimum amount of protein necessary to completely coat the particles. The amount of minimum protein used depends upon the molecular mass of the protein (i.e., its hydrodynamic radius), the size (surface area) of the nanoparticle, and the concentration of nanoparticles. For example, when 20 nm gold nanoparticles are used at about 6 to $6.5 \times 10^{11}$ particles per mL, about 2.5 µg/mL of a protein of about 50 to 150 kDa is sufficient to fully coat the nanoparticles. Therefore, protein in excess of 2.5 µg/mL is used for each sample of the plurality of samples under those conditions. Here, for example protein in included in a sample at about 2.6 µg/mL-about 512 µg/mL or more, about 3±1 µg/mL, about 4±1 µg/mL, about 5±1 µg/mL, about 6±1 µg/mL, about 7±1 µg/mL, about 8±1 µg/mL, about 9±1 µg/mL, about 10±1 µg/mL, about 15±5 µg/mL, about 20±5 µg/mL, about 25±5 µg/mL, about 30±5 µg/mL, about 40±5 µg/mL, about 50±10 µg/mL, about 60±10 µg/mL, about 70±10 µg/mL, about 80±10 µg/mL, about 90±10 µg/mL, about 100±10 µg/mL, about 125±15 µg/mL, about 150±25 µg/mL, 175±25 µg/mL, 200±25 µg/mL, 225±25 µg/mL, 250±25 µg/mL, 300±50 µg/mL, 350±50 µg/mL, 400±50 µg/mL, 450±50 µg/mL, 500±50 µg/mL or 512±50 µg/mL. In some embodiments, the plurality of samples includes two samples, three samples, four samples, five samples, six samples, seven samples, eight samples, nine samples, 10 samples or more containing a different protein concentration.

For example, the plurality of samples in one embodiment includes $6.3 \times 10^{11}$ particles/mL 20 nm gold nanoparticles and an antibody at a first concentration of about 3.125 µg/mL, a second concentration of 6.25 µg/mL, a third concentration of about 12.5 µg/mL, a fourth concentration of about 25 µg/mL, a fifth concentration of about 50 µg/mL, a sixth concentration of about 100 µg/mL, a seventh concentration of about 200 µg/mL, and an eighth concentration of about 400 µg/mL.

In one embodiment, for each sample in the plurality of samples used to determine multiple individual absorbance intensity ratio values for a given subject protein, each nanoparticle/protein combination is combined with a variable salt concentration. For example, the sample may contain a neutral salt protein, like sodium chloride, at a concentration of about 1 µM, about 10 µM, about 100 µM, about 1 mM, about 2 mM, about 4 mM, about 6 mM, about 8 mM, about 10 mM, about 20 mM, about 30 mM, about 40 mM, about 50 mM, about 60 mM, about 70 mM, about 80 mM, about 90 mM, about 100 mM, about 150 mM, about 175 mM, about 200 mM, about 250 mM or about 300 mM or more. In another embodiment, the salt may be a chaotropic salt, such as guanidinium chloride, lithium perchlorate, lithium acetate, magnesium chloride or the like. The sample may also contain in addition to or in lieu of the chaotropic salt another chaotropic agent such as butanol, ethanol, phenol, propanol, sodium dodecyl sulfate, thiourea or urea. In another embodiment, the sample may contain a kosmotropic salt such as a salt of carbonate, sulfate or phosphate, for example ammonium sulfate.

The plurality of samples may contain two, three, four, five, six, seven, eight, nine or 10 or more subsets of samples having a different salt concentration. Thus for example, a plurality of samples may comprise 10 different protein concentrations at three different salt concentrations for a total of 30 samples. In a specific embodiment, one subset of the plurality of samples contains about 2 mM sodium chloride, another set of the plurality of samples contains about 20 mM sodium chloride, and another set of plurality of samples contains about 200 mM sodium chloride. 2 mM salt is considered low ionic strength and 200 mM is considered high ionic strength. High tonicity up to and including 300 mM salt, although not pertinent to most therapeutic formulations of protein, is used in the context of protein preparations undergoing purification via hydrophobic interaction chromatography (HIC) columns. Therefore the invention is useful in determining whether the high concentration protein in high concentration salt conditions will be suitable for HIC purification or the like.

The white light is applied to the each sample, and its absorbance spectrum is obtained. The absorbance intensity ratio is calculated from each sample of the plurality and plotted. In those samples in which the nanoparticles do not aggregate or wherein the aggregation is low, i.e., where the protein exhibits repulsiveness or low aggregation potential, the absorbance peak wavelength and absorbance intensity are similar to the control uncoated nanoparticles. In those samples in which the nanoparticles aggregate, i.e., where the protein exhibits attractiveness or high aggregation potential, the absorbance peak wavelength shifts toward the red and the absorbance profile flattens as the peak absorbance intensity decreases relative to the control uncoated nanoparticles.

Each sample of the plurality of samples for a given protein may exhibit different absorbance profiles (i.e., different absorbance intensity ratios), in some cases showing attractiveness and in other cases showing repulsiveness. Those proteins have a dynamic range of colloidal stability and may be colloidally stable under specific conditions. For some proteins, the protein may show repulsiveness across all parameters (samples). Such a protein is considered robust or having robust dynamic colloidal stability. For other proteins, the protein may show attractiveness under all tested parameter conditions. Such a protein is considered colloidally instable.

Figure 13:
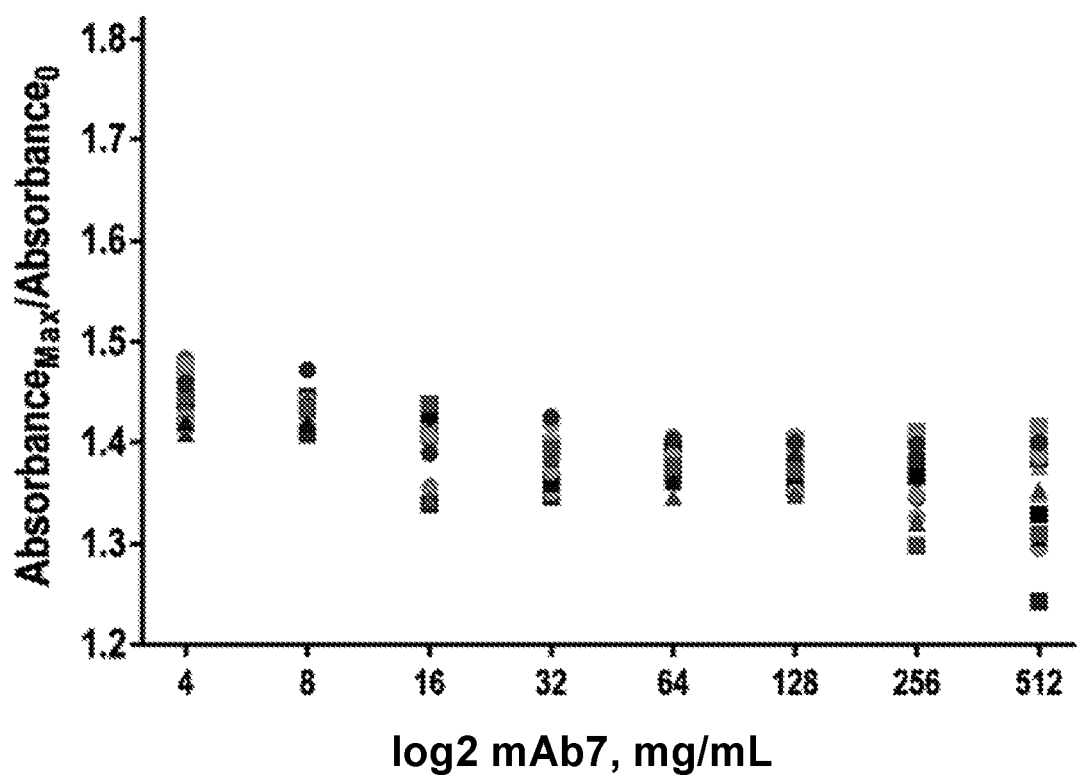
FIG. 13 depicts a CD-SINS scatter plot of absorbance intensity ratios of different concentrations of monoclonal antibody 7 (mAb7) formulated in different buffers, pHs, and ionic strengths. Each symbol represents a different buffer, pH and ionic strength formulation with variable mAb7 concentrations (X-axis).
Figure 14:
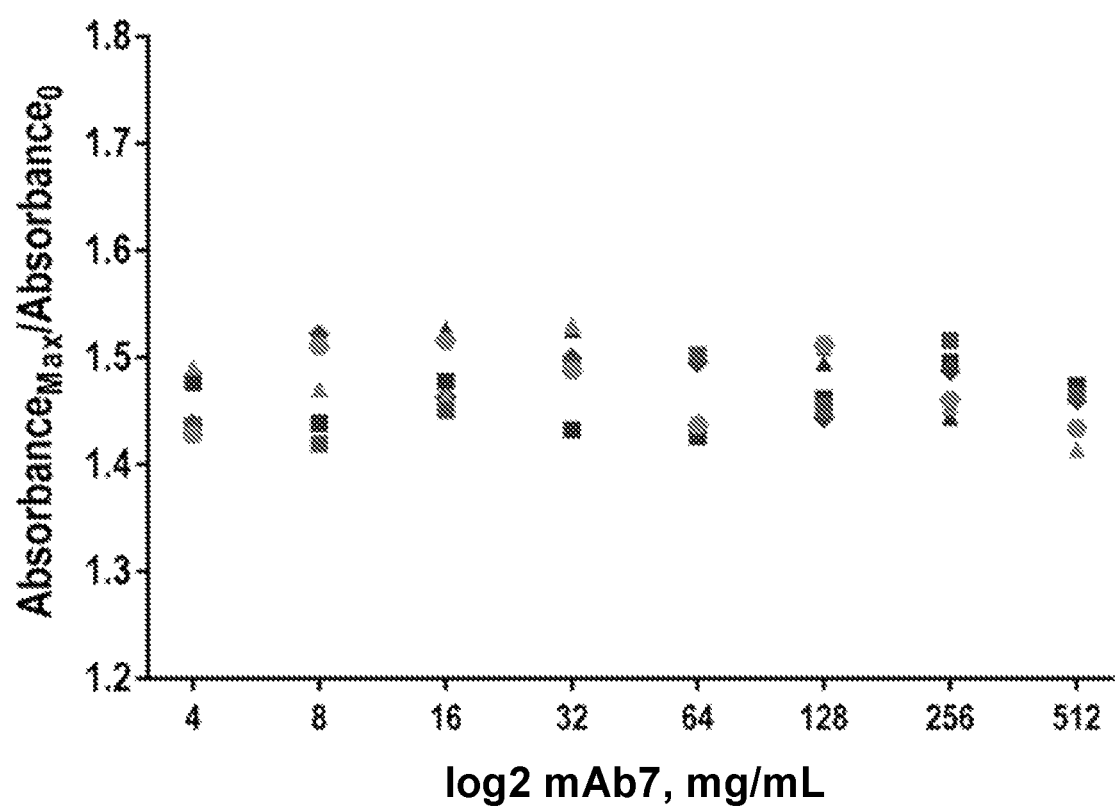
FIG. 14 depicts a CD-SINS scatter plot of absorbance intensity ratios of different concentrations of monoclonal antibody 7 (mAb7) formulated in the presence of different sugars, concentrations of sugars, and/or amino acids. Each symbol represents a different sugar/amino acid formulation with variable mAb7 concentrations (X-axis).

Those proteins that exhibit repulsiveness under at least one tested condition (in at least one sample) may be selected for large scale production and formulation as a stable drug substance. Those proteins are less likely to form aggregates during production and storage. Furthermore, those conditions under which a protein exhibits repulsiveness can inform the production steps and formulation excipients of the protein as a drug substance. For example, utilizing concentration-dependent SINS (CD-SINS) as described herein can determine manufacturability of proteins, e.g. in the downstream ultrafiltration and diafiltration steps. Selection of a low viscosity protein solution for large scale manufacturing may increase efficiency and decrease cost in bioprocessing (Shire S J, 2009, "Formulation and manufacturability of biologics." *Curr Opin Biotechnol.* 20(6):708-14). CD-SINS is also generally amenable to a wide range of excipients (both traditional and non-traditional). CD-SINS can be utilized to derive structure-activity relationships between different chemical series used for formulating the protein drug substance, and can be utilized to select for excipients that reverse self-association (see Example 11 and FIGS. 13 and 14).

Figure 3:
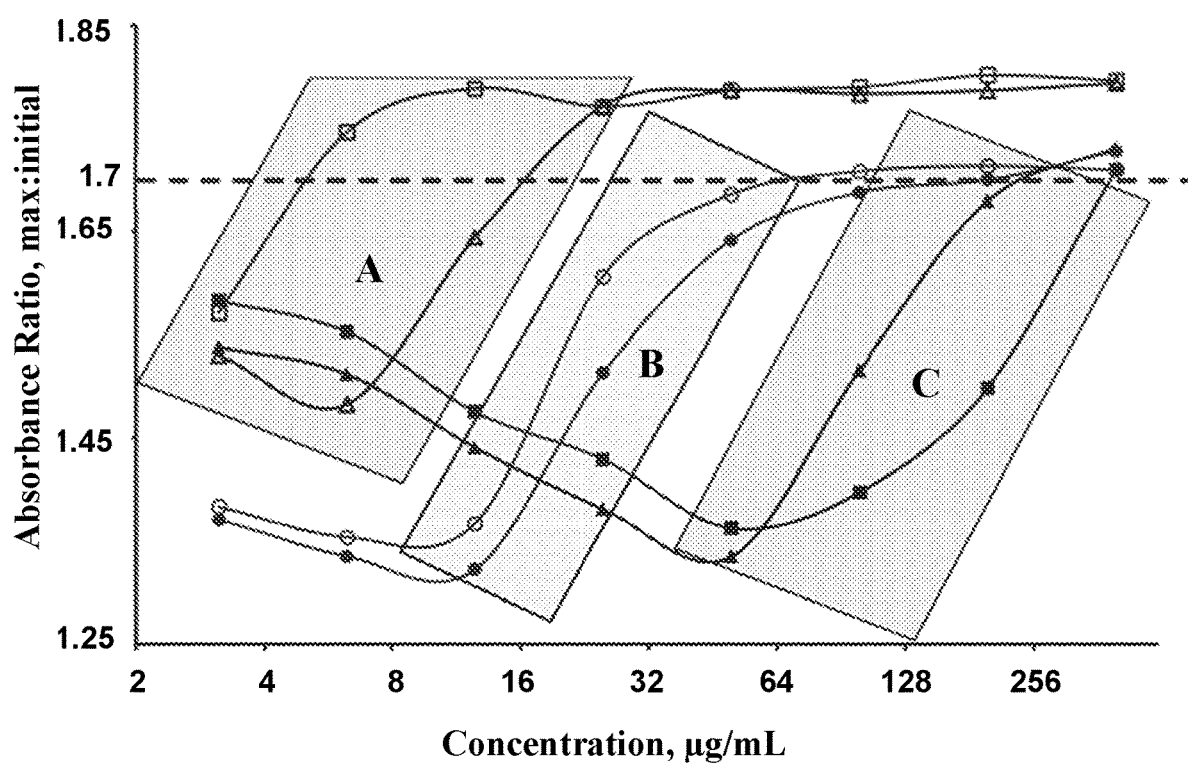

General criteria for selecting molecules and conditions having acceptable colloidal stability dynamics are depicted in FIG. 3, which plots the absorbance intensity ratio of two proteins, mAb1 and mAb5 under three ionic strength conditions. Three buckets are provided: (A) safe to proceed, which includes robust molecules expected to be stable at high concentration; (B) proceed with caution, which includes molecules showing absorbance intensity ratios above the threshold level (e.g., an $A_{peak}/A_{450}$ of ≥1.7) under some conditions; and (C) potentially problematic, which includes molecules failing to attain the threshold absorbance intensity ratio value under any condition. For example, mAb1 (open symbols) is robust in terms of colloidal stability, falling into the "safe to proceed" bucket under lower salt conditions (2 mM NaCl, open squares; 20 mM NaCl, open triangles), a "proceed with caution" category under higher salt conditions (200 mM NaCl, open circles). Conversely, mAb5 (closed symbols) is less robust, falling into the "potentially problematic" category under lower salt conditions, and the "proceed with caution" bucket under the higher salt condition.

Concentration-dependent SINS (CD-SINS) demonstrates how protein/solvent systems "evolve" with increasing protein concentration. It captures myriad colloidal interactions that different proteins exhibit at high protein concentration: repulsive to ideal (neutral); attractive to ideal; ideal to attractive; and insensitive. It captures many of the different facets of colloidal interactions such as charge mediated repulsion or attraction, tracts electrostatic screening and qualitatively provides a fairly wide dynamic range. CD-SINS reveals possible hydrophobic mediated issues and flags generally problematic molecules. The method provides an analytical tool for assessing high protein concentration developability with remarkably minimal protein requirements, and which is amenable to automation.

Reduction of Viscosity of Attractive or Mixed Colloidal Protein

Those proteins having unfavorable dynamic colloidal interaction profiles, i.e., that tend to self-associate, generally may have high viscosities at higher concentrations. Such high viscosity at high concentration may render the protein undesirable for parenteral injection. The CD-SINS assay described herein is useful to screen for viscosity-reducing excipients. In one aspect, a method for producing a reduced-viscosity protein formulation is provided. In one embodiment, a potential viscosity-reducing excipient In some embodiments, the viscosity-reducing excipient reduces the viscosity of the protein solution by at least 10%, 15%, 20%, 25%, 30%, 35%, 40%, 45%, 50%, 55%, 60%, 65%, 70%, 75%, 80%, 85%, 90%, 95%, 100%, 2.5-fold, 3-fold, 3.5-fold, 4-fold, 4.5-fold, 5-fold, or >5-fold relative to the viscosity of the protein solution without the viscosity-reducing excipient.

In some embodiments, the viscosity-reducing excipient is an amino acid or a salt of an amino acid. In some embodiments, the viscosity-reducing excipient is a hydrocarbon, an alkane, an alkene, and alkyne, a fatty acid, a fatty acid tail, a benzene-containing structure, a benzoic acid, a substituted hydrocarbon, a substituted alkane, a substituted alkene, a substituted alkyne, a substituted fatty acid, a substituted fatty acid tail, a substituted benzene-containing structure, a substituted benzoic acid, a sulfonic acid, an aminobenzoic acid, an alkylated benzoic acid, an hydroxybenzoic acid, or an ammonium salt of a benzoic acid. In one embodiment, the viscosity-reducing excipient is a para-amino benzoic acid (PABA). In one embodiment, the PABA is included in the protein formulation at a concentration of 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 21 mM, 22 mM, 23 mM, 24 mM, or 25 mM. In one embodiment, the viscosity-reducing excipient is PABA combined at a concentration of >12 mM or at a concentration of 20 mM in the protein solution.

Definitions

As used herein, the term "colloidal stability", which can be used interchangeably with "propensity to self-associate" or "propensity to aggregate", means the net (overall) effect of through-space molecular forces, for example electrostatic, van der Waals, and the like, which may result in an attractive, neutral, or repulsive interaction potential of a protein.

As used herein, the term "absorbance intensity ratio" means the ratio of the peak absorbance intensity of a sample to baseline absorbance intensity. The baseline intensity may be obtained from the absorbance of the sample at an arbitrary wavelength sufficiently shorter or longer than the expected absorbance wavelength. In some embodiments, the expected absorbance wavelength for the 20 nm gold nanoparticles ranges from about 500 to 600 nm, and peaks at about 530 nm. Therefore, the baseline absorbance intensity may be the absorbance intensity of the sample at a wavelength lower than 500 or greater than 600. For example, the baseline absorbance intensity may be the absorbance intensity of the sample at 450 nm. Here, the absorbance intensity ratio is the absorbance intensity at the peak absorbance wavelength ($A_{peak}$) of the sample divided by the absorbance intensity at 450 nm ($A_{450}$ or $A_{initial}$).

In other embodiments, the baseline absorbance intensity may be the intensity of the peak absorbance of uncoated nanoparticles (control nanoparticles). Here, the nanoparticles without protein, but in the same buffered salt in which the experimental coated nanoparticles are sampled, are subjected to absorbance analysis. The peak absorbance intensity of the uncoated control nanoparticles ($A_{control}$) serves as the baseline absorbance intensity. Here, the absorbance intensity ratio is calculated as $A_{peak}/A_{control}$.

Absorbance is generally expressed in arbitrary units, which cancel out when the ratio is calculated. Absorbance is measured by passing a white light source through a sample. The sample absorbs light of certain wavelengths at certain strengths, according to the optical properties of the sample. The intensity of light that passes through the sample, i.e., the "transmitted light", is measured at multiple wavelengths and the intensity of the "absorbed light" is calculated.

The absorbance spectrum of the gold nanoparticles is determined by the particle surface plasmon resonance. The electric field from incoming light interacts with the free electrons on the surface of gold particles and results in a strong absorption in the visible region. This optical property depends on the size, shape, and agglomeration status of the nanoparticles. For example, smaller particles (20 nm in diameter) absorb at a lower wavelength (~522 nm) and with a narrower and more intense peak (A=~0.6) than larger particles (e.g., 250 nm particle absorbs most strongly at 570-660 nm with an intensity about 40% of the intensity of the 20 nm particle). An irregularly-shaped particle shows a broader peak of lower intensity that is red-shifted relative to a spherical particle. Likewise, agglomerated particles show a broader peak of lower intensity that is red-shifted relative to discrete dispersed spherical particles (FIG. 1).

As used herein, the term "threshold value" denotes an absorbance intensity ratio above which a protein is considered to be feasible for achieving a stable high concentration in solution. A protein sample having an absorbance ratio below the threshold value indicates that the protein, at least under the experimental conditions of pH, ionic strength, and protein density, may not be feasible for achieving a stable high concentration in solution. This feasibility of a protein to achieve a high concentration in solution is inversely related to the protein's "attractiveness" or potential for self-association, and is positively related to the protein's "repulsiveness". In some embodiments, the threshold value is about 1.5, 1.6, 1.7, 1.8, 1.9, or 2 ($A_{peak}/A_{450}$). In some embodiments, the threshold value is about 0.7, 0.8, 0.9, or 1 ($A_{peak}/A_{control}$).

Figure 2:
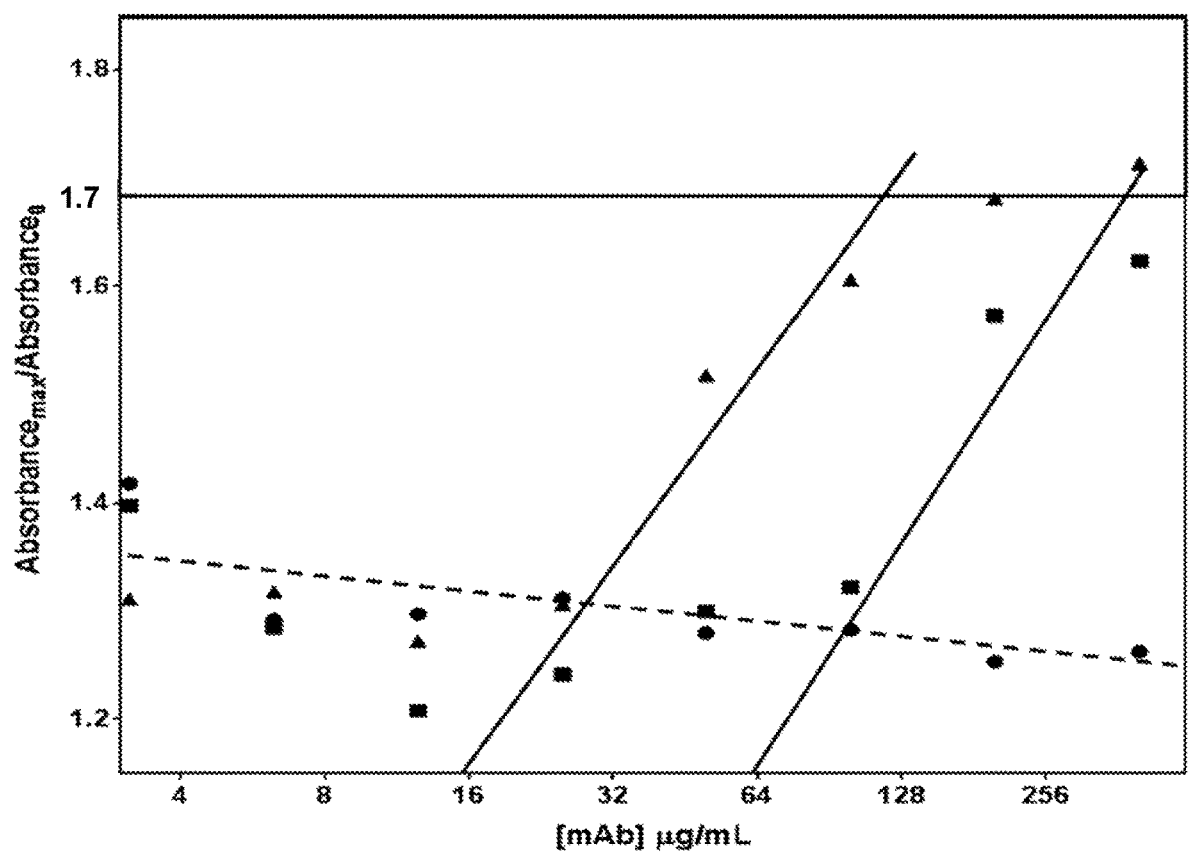

As used herein, the term "dynamic range" refers to a protein's potential for self-association over a range of conditions. Prior art self-association assays that employ self-interaction nanoparticle spectroscopy (SINS) only measure the self-association potential of proteins under a single set of conditions. A protein is deemed "attractive" under that single point assay may be rejected, whereas a protein that is deemed "repulsive" under that assay may be retained as feasible for high concentration formulation and production. Here, a series of absorbance intensity ratios are obtained under varying experimental conditions and plotted, generating a "dynamic range" profile for a particular protein. Under some conditions, the protein may have a below-threshold absorbance intensity ratio, while under other conditions the protein may have an above-threshold absorbance intensity ratio. Such a protein would have an acceptable degree of repulsiveness under those conditions, which can inform the selection of protein manufacturing processes and formulation excipients and concentrations. For example, monoclonal antibody 2 (mAb2) shows an acceptable degree of repulsiveness under high concentration/high ionic strength (e.g., 200 mM NaCl) conditions, but unacceptable attractiveness under low ionic strength conditions (FIG. 2).

Experimental conditions used to determine the dynamic range of the protein include the concentration of the protein; the size, shape number of nanoparticle; the material from which the nanoparticle is made; the method of coating the nanoparticles with protein; the nature and amounts of ingredients in the buffer or solvent; the pH; and the ionic strength of the solution. For example, the pH of the buffer may affect the overall charge of the protein depending on the protein's isoelectric point (pI), and the charge in turn may affect the second order virial coefficient of the protein (negative $B_{22}$ is attractive, and a positive $B_{22}$ is repulsive). Ionic strength (i.e., salt content) is generally known to affect protein self-attraction, where increasing ionic strength shields proteins against charge-based repulsion and promotes attraction.

In some embodiments, data points (i.e., absorbance intensity ratios) are taken at different salt concentrations or with no salt at all. For example, the salt, e.g., sodium chloride, may be included at any concentration ranging from trace amounts to supersaturated. In some embodiments, sodium chloride is included in the "buffered salt" at a concentration of about 0.1 mM to about 1 M, 1 mM to 500 mM, or 2 mM to 300 mM. In some embodiments, data points are taken at two, three, four, five, six, seven, eight, nine, 10 or more different salt concentration conditions. In one embodiment, at least three salt concentration conditions are used, for example 2 mM, 20 mM and 200 mM sodium chloride. In another embodiment, at least five salt concentration conditions are used. Non-limiting examples of five salt concentration conditions may include: 1 mM, 2 mM, 20 mM, 200 nM and 300 mM sodium chloride, or 1 mM, 5 mM, 20 mM, 100 nM and 300 mM sodium chloride. The skilled artisan may readily adapt the assay by using different salts and/or salt conditions based on the nature of the experimental or therapeutic use of the protein of interest.

As used herein, the term "buffered salt" denotes an aqueous solution containing a buffer and a salt. The salt may be at any concentration, and the buffer may have buffering capacity at any range of pH. In some embodiments, the salt and the buffer may be one and the same, such as calcium carbonate. Salts are known to affect protein interaction and are often used to precipitate proteins, to affect protein folding, to stabilize pharmaceutical formulations, to provide tonicity, and to regulate protein behavior during chromatography. Salts may be kosmotropic (positive free energy of hydrogen bonding) or chaotropic (negative free energy of hydrogen bonding) agents. Kosmotropes facilitate water-water interactions and are commonly used to salt-out proteins. Examples of kosmotropic ions include carbonate, sulfate, phosphate, magnesium, lithium, zinc and aluminum. Chaotropes disrupt hydrogen bonding and weaken hydrophobic effects, thereby promoting protein denaturation. Examples of chaotropic salts include guanidinium chloride, lithium perchlorate, lithium acetate and magnesium chloride. Salts like sodium chloride are near the middle of the Hofmeister series, meaning that they are neither effective at salting-in nor salting-out. Depending on the objective of the protein self-association assay, salts of the buffered salt may be selected for their ability to salt-in, salt-out or remain effectively neutral at physiological concentrations.

"Buffers" are included to control pH, which in turn affects the charge properties of proteins, and subsequent structure and function. Depending on the objective of the protein self-association assay, buffers may be selected for example for their ability to enhance protein purification, promote long term protein stability or allow for patient comfort during administration of a therapeutic protein. Useful buffers are well-known in the art and include MES, TRIS, PIPES, MOPS, phosphate, citrate-phosphate, citrate, acetate, carbonate-bicarbonate, histidine, imidazole and the like. In one particular embodiment, the buffer used in the protein self-association assay is MES (2-(N-morpholino) ethanesulfonic acid), which has a useful buffer range of about pH 5.5 to 6.7. In a specific embodiment, the MES is included in the buffered salt at about 10 mM, pH6.

A buffer is used in the buffered salt component of the assay system and reagents. A buffer is also used to control the pH of solutions that contain the protein beyond the assay. Buffers are used in cell culture production media used to produce the protein. Buffers are also used in solutions used during protein purification and the various unit operations deployed therein. Buffers are used in formulated drug substances and in the final drug product formulation.

Buffers useful in the formulation of proteins are well known in the art and include histidine, succinate, citrate, acetate, phosphate and the like. The buffer may be included in the formulated drug substance (FDS) or drug product (DP) at a concentration of from 1 mM to 100 mM. In some particular embodiments, the buffer is included at about 10 mM. In certain embodiments, the buffer is present at a concentration of 5 mM±0.75 mM to 15 mM±2.25 mM; 6 mM±0.9 mM to 14 mM±2.1 mM; 7 mM±1.05 mM to 13 mM±1.95 mM; 8 mM±1.2 mM to 12 mM±1.8 mM; 9 mM±1.35 mM to 11 mM±1.65 mM; 10 mM±1.5 mM; or about 10 mM. In some specific embodiments, the buffer system of the FDS or DP comprises histidine, phosphate, and/or acetate at 10 mM±1.5 mM.

In some embodiments, the buffer is selected from a chemical capable of buffering somewhere within the pH range of about 3 to about 9, or within the pH range of about 3.7 to about 8.0. For example, the pre-lyophilized solution may have a pH of about 3.4, about 3.6, about 3.8, about 4.0, about 4.2, about 4.4, about 4.6, about 4.8, about 5.0, about 5.2, about 5.4, about 5.6, about 5.8, about 6.0, about 6.2, about 6.4, about 6.6, about 6.8, about 7.0, about 7.2, about 7.4, about 7.6, about 7.8, or about 8.0.

The buffer may be a combination of individual buffers, such as, e.g., the combination of histidine and acetate (his-acetate buffer). In one embodiment, the buffer has a buffering range of about 3.5 to about 6, or about 3.7 to about 5.6, such as the range buffered by acetate. In one embodiment, the buffer has a buffering range of about 5.5 to about 8.5, or about 5.8 to about 8.0, such as the range buffered by phosphate. In one embodiment, the buffer has a buffering range of about 5.0 to about 8.0, or about 5.5 to about 7.4, such as the range buffered by histidine.

As used herein, the term "nanoparticle" refers to a spherical, near spherical or spheroidal particle having a diameter on the scale of $10^{-9}$ M (0.001 micron) to $10^{-6}$ M (1 micron). Nanoparticles may comprise any material, including organic polymers, metals, semiconductor materials, magnetic materials and combinations of materials. Metal nanoparticles are particularly suitable for surface plasmon resonance-based assays, since metal spheres have free electrons on their surface that can interact with the electric field from incident light, resulting in a strong absorbance spectrum. Gold nanoparticles and silver nanoparticles are examples of metal nanoparticles useful for measuring changes in plasmon resonance. The size, shape and material of the nanoparticle affects the intensity and wavelength of maximum absorbance. Gold nanoparticles of 20 nm to 400 nm diameter are useful. In some embodiments, the nanoparticle used in the self-association dynamic range assay is a gold nanoparticle (AuNP) with a diameter of about 20 nm, 30 nm, 40 nm, 50 nm, 60 nm, 80 nm or 100 nm.

As used herein, the term "light" means electromagnetic radiation (EMR). The light can be of a single wavelength, of a narrow range of wavelengths, of a broad range of wavelengths such as "white light", of a collection of wavelengths. The light can be in the form of a laser beam or as diffused light. The self-aggregation assay is a spectrophotometric assay, where the affect that the sample has on light is measured. Thus, light is applied to the sample (i.e., "incident light"), the sample interacts with the light, such as generating plasmons and absorbing particular wavelengths of light (i.e., absorbed light), and a subset of the light is transmitted through the sample and on to a detector (i.e., "transmitted light"). In some embodiments, the incident light is a white light comprising EMR having wavelengths of 400 nm to 800 nm. In some embodiments, transmitted light is detected and measured at wavelengths spanning 400 nm to 800 nm, from which the absorbance intensity is determined.

As used herein, the term "self-associate" refers to the non-specific binding of a specific protein to another protein of the same species. By non-specific, what is meant is association by weak forces that are considered to by non-biological. To distinguish non-specific from specific interaction, the association of two identical antibody halves to form an intact antibody is considered a specific interaction. Conversely, the associations of two or more identical intact antibodies via Van der Waals or hydrophobic interactions to form dimers, trimers or higher order multimers that are reversible or irreversible are "non-specific".

As used herein, the term "stable" or "stability" refers to the retention of an acceptable degree of physical structure (thermodynamic stability), chemical structure (kinetic stability), or biological function (functional stability) of a protein or other biological macromolecule over time. The protein may be stable even though it does not maintain 100% of its physical structure, chemical structure, or biological function after storage for a certain amount of time. Under certain circumstances, maintenance of about 90%, about 95%, about 96%, about 97%, about 98% or about 99% of the protein's structure or function after storage for a particular amount of time may be regarded as "stable".

Stability may be measured by determining the percentage of native protein remaining in a sample. The percentage of protein that retains its native form may be determined by size exclusion chromatography, which separates high molecular weight aggregates of the protein form the lower molecular weight native protein. A stable protein will retain 90% or more of its native structure over time. A stable protein contains no more than 10% of the total protein species as an irreversible aggregate.

A stable protein has a low rate of aggregate formation. A stable protein undergoes an increase in the formation of high molecular weight species, i.e., aggregation, that is less than 15%, less than 14%, less than 13%, less than 12%, less than 11%, less than 10%, less than 9%, less than 8%, less than 7%, less than 6%, less than 5%, less than 4%, less than 3%, less than 2%, less than 1%, or less than 0.5% during storage at about 5° C. to about 25° C. for up to 7 months, up to 8 months, up to 9 months, up to 10 months, up to 11 months, up to 12 months, up to 13 months, up to 14 months, up to 15 months, up to 16 months, up to 17 months, up to 18 months, up to 19 months, up to 20 months, up to 21 months, up to 22 months, up to 23 months, or up to 24 months.

Other methods may be used to assess the stability of a protein such as, e.g., differential scanning calorimetry (DSC) to determine thermal stability, controlled agitation to determine mechanical stability, and absorbance at about 350 nm or about 405 nm to determine solution turbidities. In one embodiment, a protein may be considered stable if after storage for 6 months or more at about 5° C. to about 25° C., the change in OD405 of the formulation is less than about 0.05 (e.g., 0.04, 0.03, 0.02, 0.01, or less) from the OD405 of the protein at time zero.

As used herein, the term "protein" means any amino acid polymer having more than about 50 amino acids covalently linked via amide bonds. Proteins contain one or more amino acid polymer chains known in the art as "polypeptides". A protein may contain one or more polypeptides to form a single functioning biomolecule. "Polypeptides" generally contain over 50 amino acids, whereas "peptides" generally contain 50 amino acids or less. Proteins may contain one or more covalent and non-covalent modifications. Disulfide bridges (i.e., between cysteine residues to form cysteine) may be present in some proteins. These covalent links may be within a single polypeptide chain, or between two individual polypeptide chains. For example, disulfide bonds are essential to proper structure and function of insulin, immunoglobulins, protamine, and the like. For a recent review of disulfide bond formation, see Oka and Bulleid, "Forming disulfides in the endoplasmic reticulum," 1833(11) Biochim Biophys Acta 2425-9 (2013).

In addition to disulfide bond formation, proteins may be subject to other post-translational modifications. Those modifications include lipidation (e.g., myristoylation, palmitoylation, farnesoylation, geranylgeranylation, and glycosylphosphatidylinositol (GPI) anchor formation), alkylation (e.g., methylation), acylation, amidation, glycosylation (e.g., addition of glycosyl groups at arginine, asparagine, cysteine, hydroxylysine, serine, threonine, tyrosine, and/or tryptophan), and phosphorylation (i.e., the addition of a phosphate group to serine, threonine, tyrosine, and/or histidine). For a recent review on the post-translational modification of proteins produced in eukaryotes, see Mowen and David, "Unconventional post-translational modifications in immunological signaling," 15(6) Nat Immunol 512-20 (2014); and Blixt and Westerlind, "Arraying the post-translational glycoproteome (PTG)," 18 Curr Opin Chem Biol. 62-9 (2014).

Examples of proteins include therapeutic proteins, recombinant proteins used in research or therapy, trap proteins and other receptor Fc-fusion proteins, chimeric proteins, antibodies, monoclonal antibodies, human antibodies, bispecific antibodies, antibody fragments, nobodies, recombinant antibody chimeras, cytokines, chemokines, peptide hormones, and the like. Proteins may be produced using recombinant cell-based production systems, such as the insect bacculovirus system, yeast systems (e.g., *Pichia* sp.), mammalian systems (e.g., CHO cells and CHO derivatives like CHO-K1 cells). For a recent review discussing therapeutic proteins and their production, see Ghaderi et al., "Production platforms for biotherapeutic glycoproteins. Occurrence, impact, and challenges of non-human sialylation," 28 Biotechnol Genet Eng Rev. 147-75 (2012).

As used herein, the term "antigen-binding protein" denotes any protein that binds another molecular entity. The molecular entity may be a peptide, polypeptide, protein, epitope, hapten, antigen or biological molecule. For example, an antigen-binding protein includes a receptor molecule that binds a ligand, where the ligand is the antigen. Antigen-binding proteins include antibodies, antibody fragments (e.g., Fabs), single-chain antibodies, ScFv molecules, recombinant proteins comprising receptors and parts of receptors, ligand molecules, recombinant proteins comprising ligands or parts of ligands, recombinant molecules comprising multiple receptors or receptor fragments (e.g., receptor-Fc-fusion proteins), and the like.

"Antibody" or "immunoglobulin molecule" is a subset or subtype of an antigen-binding protein. The canonical immunoglobulin protein (e.g., IgG) comprises four polypeptide chains, two heavy (H) chains and two light (L) chains inter-connected by disulfide bonds. Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3. As used herein, "monoclonal antibody" merely means an antibody of single molecular entity, usually produced by clones of a parent cell that produces a single antibody. Monoclonal antibodies are distinguished from polyclonal antibodies by the fact that polyclonal antibodies represent a collection of antibodies made by different cells. A monoclonal antibody may have monovalent affinity, meaning that both antibody halves are identical and bind to the same epitope, or bivalent affinity, as in a "bispecific antibody", meaning that one antibody half binds a different epitope than the other antibody half.

"Bispecific antibody" includes any antibody capable of selectively binding two or more epitopes. Bispecific antibodies generally comprise two different heavy chains, with each heavy chain specifically binding a different epitope, either on two different molecules (e.g., antigens) or on the same molecule (e.g., on the same antigen). If a bispecific antibody is capable of selectively binding two different epitopes (a first epitope and a second epitope), the affinity of the first heavy chain for the first epitope will generally be at least one to two or three or four orders of magnitude lower than the affinity of the first heavy chain for the second epitope, and vice versa. The epitopes recognized by the bispecific antibody can be on the same or a different target (e.g., on the same or a different protein). Bispecific antibodies can be made, for example, by combining heavy chains that recognize different epitopes of the same antigen. For example, nucleic acid sequences encoding heavy chain variable sequences that recognize different epitopes of the same antigen can be fused to nucleic acid sequences encoding different heavy chain constant regions, and such sequences can be expressed in a cell that expresses an immunoglobulin light chain. A typical bispecific antibody has two heavy chains each having three heavy chain CDRs, followed by (N-terminal to C-terminal) a CHI domain, a hinge, a CH2 domain, and a CH3 domain, and an immunoglobulin light chain that either does not confer antigen-binding specificity but that can associate with each heavy chain, or that can associate with each heavy chain and that can bind one or more of the epitopes bound by the heavy chain antigen-binding regions, or that can associate with each heavy chain and enable binding or one or both of the heavy chains to one or both epitopes.

The phrase "heavy chain," or "immunoglobulin heavy chain" includes an immunoglobulin heavy chain constant region sequence from any organism, and unless otherwise specified includes a heavy chain variable domain. Heavy chain variable domains include three heavy chain CDRs and four FR regions, unless otherwise specified. Fragments of heavy chains include CDRs, CDRs and FRs, and combinations thereof. A typical heavy chain has, following the variable domain (from N-terminal to C-terminal), a CH1 domain, a hinge, a CH2 domain, and a CH3 domain. A functional fragment of a heavy chain includes a fragment that is capable of specifically recognizing an antigen (e.g., recognizing the antigen with a KD in the micromolar, nanomolar, or picomolar range), that is capable of expressing and secreting from a cell, and that comprises at least one CDR.

The phrase "light chain" includes an immunoglobulin light chain constant region sequence from any organism, and unless otherwise specified includes human kappa and lambda light chains. Light chain variable (VL) domains typically include three light chain CDRs and four framework (FR) regions, unless otherwise specified. Generally, a full-length light chain includes, from amino terminus to carboxyl terminus, a VL domain that includes FR1-CDR1-FR2-CDR2-FR3-CDR3-FR4, and a light chain constant domain. Light chains that can be used with this invention include those, e.g., that do not selectively bind either the first or second antigen selectively bound by the antigen-binding protein. Suitable light chains include those that can be identified by screening for the most commonly employed light chains in existing antibody libraries (wet libraries or in silico), where the light chains do not substantially interfere with the affinity and/or selectivity of the antigen-binding domains of the antigen-binding proteins. Suitable light chains include those that can bind one or both epitopes that are bound by the antigen-binding regions of the antigen-binding protein.

The phrase "variable domain" includes an amino acid sequence of an immunoglobulin light or heavy chain (modified as desired) that comprises the following amino acid regions, in sequence from N-terminal to C-terminal (unless otherwise indicated): FR1, CDR1, FR2, CDR2, FR3, CDR3, FR4. A "variable domain" includes an amino acid sequence capable of folding into a canonical domain (VH or VL) having a dual beta sheet structure wherein the beta sheets are connected by a disulfide bond between a residue of a first beta sheet and a second beta sheet.

The phrase "complementarity determining region," or the term "CDR," includes an amino acid sequence encoded by a nucleic acid sequence of an organism's immunoglobulin genes that normally (i.e., in a wild-type animal) appears between two framework regions in a variable region of a light or a heavy chain of an immunoglobulin molecule (e.g., an antibody or a T cell receptor). A CDR can be encoded by, for example, a germline sequence or a rearranged or unrearranged sequence, and, for example, by a naive or a mature B cell or a T cell. In some circumstances (e.g., for a CDR3), CDRs can be encoded by two or more sequences (e.g., germline sequences) that are not contiguous (e.g., in an unrearranged nucleic acid sequence) but are contiguous in a B cell nucleic acid sequence, e.g., as the result of splicing or connecting the sequences (e.g., V-D-J recombination to form a heavy chain CDR3).

Fc-containing proteins include antibodies, bispecific antibodies, immunoadhesins, "receptor-Fc-fusion proteins" and other binding proteins that comprise at least a functional portion of an immunoglobulin CH2 and CH3 region. A "functional portion" refers to a CH2 and CH3 region that can bind an Fc receptor (e.g., an FcγR; or an FcRn, i.e., a neonatal Fc receptor), and/or that can participate in the activation of complement. If the CH2 and CH3 region contains deletions, substitutions, and/or insertions or other modifications that render it unable to bind any Fc receptor and also unable to activate complement, the CH2 and CH3 region is not functional.

Fc-containing proteins can comprise modifications in immunoglobulin domains, including where the modifications affect one or more effector function of the binding protein (e.g., modifications that affect FcγR binding, FcRn binding and thus half-life, and/or CDC activity). Such modifications include, but are not limited to, the following modifications and combinations thereof, with reference to EU numbering of an immunoglobulin constant region: 238, 239, 248, 249, 250, 252, 254, 255, 256, 258, 265, 267, 268, 269, 270, 272, 276, 278, 280, 283, 285, 286, 289, 290, 292, 293, 294, 295, 296, 297, 298, 301, 303, 305, 307, 308, 309, 311, 340, 342, 344, 356, 358, 359, 360, 361, 362, 373, 375, 376, 378, 380, 382, 383, 384, 386, 388, 389, 398, 414, 416, 419, 428, 430, 433, 434, 435, 437, 438, and 439.

For example, and not by way of limitation, the binding protein is an Fc-containing protein and exhibits enhanced serum half-life (as compared with the same Fc-containing protein without the recited modification(s)) and have a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at 428 and/or 433 (e.g., L/R/SI/P/Q or K) and/or 434 (e.g., H/F or Y); or a modification at 250 and/or 428; or a modification at 307 or 308 (e.g., 308F, V308F), and 434. In another example, the modification can comprise a 428L (e.g., M428L) and 434S (e.g., N434S) modification; a 428L, 259I (e.g., V259I), and a 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); a 307 and/or 308 modification (e.g., 308F or 308P).

Some recombinant Fc-containing proteins contain receptors or receptor fragments, ligands or ligand fragments that have cognate binding partners in biological systems. "Receptor Fc-fusion proteins" refer to recombinant molecules that contain a soluble receptor fused to an immunoglobulin Fc domain. Some receptor Fc-fusion proteins may contain ligand binding domains of multiple different receptors. Those receptor Fc-fusion proteins are known as "traps" or "trap molecules". Rilonocept and aflibercept are examples of marketed traps that antagonize IL1R (see U.S. Pat. No. 7,927,583) and VEGF (see U.S. Pat. No. 7,087, 411), respectively. Other recombinant Fc-containing proteins include those recombinant proteins containing a peptide fused to an Fc domain, for example Centocor's MIMETIBODY™ technology. Recombinant Fc-containing proteins are described in C. Huang, "Receptor-Fc fusion therapeutics, traps, and MIMETIBODY technology," 20(6) Curr. Opin. Biotechnol. 692-9 (2009).

As used herein, the term "tonicifier" or "tonicifying agent" is a substance or combination of substances that provides tonicity or osmolality to a formulation or solution. The formulation may require a physiological osmolarity, which is approximately 0.29 osmoles of solute per kilogram of solvent (290 mOsm). A formulation having a physiological osmolality is generally referred to as physiologically isotonic. A formulation may have an osmolality lower than 290 mOsm (physiologically hypotonic) or higher than 290 mOsm (physiologically hypertonic). A tonicifier is added to a formulation to adjust the formulation to the appropriate tonicity. The term "tonicity" may be used interchangeably with osmolality or osmolarity.

Tonicifiers include salts, which are added to adjust ionic strength or conductance, and non-salt tonicifiers. Commonly used salts include sodium chloride, potassium chloride, magnesium chloride, and calcium chloride. Non-salt tonicifiers include sugars, sugar alcohols, monosaccharides, and disaccharides, examples of which include sorbitol, mannitol, sucrose, trehalose, glycerol, maltose, and lactose.

As used herein, the term "surfactant" denotes an additive or excipient that reduces interfacial surface tension. Some surfactants have a lipophilic portion and a hydrophilic portion. Surfactants are believed to provide additional stability by reducing protein-protein hydrophobic interaction and the resulting formation of high molecular weight species (i.e., aggregates). One or more surfactants may be included in protein-containing solutions, including FDSs, DPs, protein processing and manufacturing solutions, and protein self-association assay solutions. Surfactants may be ionic or non-ionic. Non-ionic surfactants include, e.g., alkyl poly (ethylene oxide), alkyl polyglucosides (e.g., octyl glucoside and decyl maltoside), fatty alcohols such as cetyl alcohol and oleyl alcohol, cocamide MEA, cocamide DEA, and cocamide TEA. Specific non-ionic surfactants include, e.g., polyoxyethylene sorbitan esters (a.k.a. polysorbates) such as polysorbate 20, polysorbate 28, polysorbate 40, polysorbate 60, polysorbate 65, polysorbate 80, polysorbate 81, and polysorbate 85; poloxamers such as poloxamer 188, poloxamer 407; polyethylene-polypropylene glycol; or polyethylene glycol (PEG). Polysorbate 20 is also known as TWEEN 20, sorbitan monolaurate and polyoxyethylenesorbitan monolaurate. Polysorbate 80 is also known as TWEEN 80, sorbitan monooleate and polyoxyethylenesorbitan monooleate.

The amount of surfactant contained within a protein-containing solution may vary depending on the specific properties and purposes desired of the solution. In certain embodiments, the solution may contain about 0.001% (w/v) to about 0.5% (w/v) surfactant (e.g., polysorbate 20 or polysorbate 80). For example, solution may contain about 0.001%; about 0.0015%; about 0.002%; about 0.0025%; about 0.003%; about 0.0035%; about 0.004%; about 0.0045%; about 0.005%; about 0.0055%; about 0.006%; about 0.0065%; about 0.007%; about 0.0075%; about 0.008%; about 0.0085%; about 0.009%; about 0.0095%; about 0.01%; about 0.015%; about 0.016%; about 0.017%; about 0.018%; about 0.019%; about 0.02%; about 0.021%; about 0.022%; about 0.023%; about 0.024%; about 0.025%; about 0.026%; about 0.027%; about 0.028%; about 0.029%; about 0.03%; about 0.031%; about 0.032%; about 0.033%; about 0.034%; about 0.035%; about 0.036%; about 0.037%; about 0.038%; about 0.039%; about 0.04%; about 0.041%; about 0.042%; about 0.043%; about 0.044%; about 0.045%; about 0.046%; about 0.047%; about 0.048%; about 0.049%; about 0.05%; about 0.051%; about 0.052%; about 0.053%; about 0.054%; about 0.055%; about 0.056%; about 0.057%; about 0.058%; about 0.059%; about 0.06%; about 0.061%; about 0.062%; about 0.063%; about 0.064%; about 0.065%; about 0.066%; about 0.067%; about 0.068%; about 0.069%; about 0.07%; about 0.071%; about 0.072%; about 0.073%; about 0.074%; about 0.075%; about 0.076%; about 0.077%; about 0.078%; about 0.079%; about 0.08%; about 0.081%; about 0.082%; about 0.083%; about 0.084%; about 0.085%; about 0.086%; about 0.087%; about 0.088%; about 0.089%; about 0.09%; about 0.091%; about 0.092%; about 0.093%; about 0.094%; about 0.095%; about 0.096%; about 0.097%; about 0.098%; about 0.099%; about 0.10%; about 0.15%; about 0.20%; about 0.25%; about 0.30%; about 0.35%; about 0.40%; about 0.45%; or about 0.50% surfactant (e.g., polysorbate 20 or polysorbate 80).

As used herein, the term "stabilizer" denotes a molecule or compound, or a combination of chemical entities (i.e., more than one chemical entity) that serves to stabilize the native conformation of the protein. Stabilizers stabilize proteins in solution through one or more of the following mechanisms: (1) increasing the surface tension of water, (2) protein-excipient exclusion which forms a layer of water around the protein, (3) negative peptide bond interaction, and (4) repulsive interaction with the surface of the protein. Regardless of the specific mechanism, stabilizers are preferentially excluded from the protein surface, thereby enriching water at the protein surface. Also, the unfavorable protein-excipient interaction renders protein unfolding thermodynamically unfavorable, since the surface area of the protein increases during denaturation. Stabilizers include e.g., polyols, sugars, amino acids, salting out salts, or any combination thereof. Examples of useful stabilizers include polyethylene glycol, sorbitol, glycerol, mannitol, trehalose, sucrose, arginine, alanine, proline, glycine, sodium chloride, or any combination thereof. Sucrose and trehalose are the most frequently used sugars.

The present invention is further described by the following non-limiting items.

Item 1. A method for determining the potential of a protein to self-associate, the method comprising:
a. combining a protein, a nanoparticle, and a buffered salt to form a sample;
b. exciting the sample with light;
c. measuring the light transmitted through the sample;
d. calculating the absorbance intensity ratio of the sample, wherein the protein is stable at high concentration when the absorbance intensity ratio exceeds a threshold value.

Item 2. The method of item 1, wherein the protein is an antigen-binding protein.

Item 3. The method of item 2, wherein the antigen-binding protein is an antibody, an antibody fragment, or a receptor-Fc-fusion protein.

Item 4. The method of item 3, wherein the antigen-binding protein is a human monoclonal antibody.

Item 5. The method according to any one of the preceding items, wherein the protein is in the sample at a concentration of about 2 μg/mL to about 512 μg/mL.

Item 6. The method according to any one of the preceding items, wherein the nanoparticle is a gold nanoparticle.

Item 7. The method of item 6, wherein the gold nanoparticle has a diameter of about 20 nm to about 100 nm.

Item 8. The method of item 7, wherein the diameter of the gold nanoparticle is about 20 nm.

Item 9. The method according to any one of the preceding items, wherein the sample comprises about $5 \times 10^{11}$ to about $8 \times 10^{11}$ nanoparticles per mL.

Item 10. The method according to any one of the preceding items, wherein sample comprises about $6$-$6.5 \times 10^{11}$ nanoparticles per mL.

Item 11. The method according to any one of the preceding items, wherein the salt is present in the sample at a concentration of about 2 mM to about 250 mM.

Item 12. The method according to any one of the preceding items, wherein the salt is sodium chloride.

Item 13. The method according to any one of the preceding items, wherein the salt concentration is about 2 mM, about 20 mM, or about 200 mM.

Item 14. The method according to any one of the preceding items, wherein the transmitted light is measured at multiple wavelengths ranging from about 450 nm to about 750 nm.

Item 15. The method according to any one of the preceding items, wherein the absorbance intensity ratio is the ratio of the absorbance maximum to the initial absorbance.

Item 16. The method according to any one of the preceding items, wherein the threshold value of the absorbance intensity ratio is about 1.7.

Item 17. The method according to any one of the preceding items further comprising repeating steps (a)-(d) using a different concentration of protein in the sample.

Item 18. The method according to any one of the preceding items further comprising repeating steps (a)-(d) using a different concentration of salt in the sample.

Item 19. The method according to any one of the preceding items further comprising repeating steps (a)-(d) using a different pH of the sample.

Item 20. The method according to any one of the preceding items further comprising:
e. combining the highly soluble protein at a high concentration with an excipient to form a formulated drug substance.

Item 21. The method according to any one of the preceding items, wherein the concentration of the protein is about 50 mg/mL to about 500 mg/mL.

Item 22. The method of according to any of items 20 or 21, wherein the excipient is selected from the group consisting of a tonicifier, a buffer, a surfactant, stabilizer, and a combination thereof.

Item 23. The method of item 22, wherein the tonicifier is a salt.

Item 24. The method according to any one of the preceding items, wherein the salt is NaCl.

Item 25. A composition comprising a biotherapeutic drug obtainable by the method according to any of the preceding claims.

Item 26. The composition according to item 25, wherein no more than about 10% of the total biotherapeutic drug species is present as an irreversible aggregate at the concentration of the biotherapeutic drug.

Item 27. The composition according to any of items 25-26, wherein the composition is such that the threshold value is in range of e.g. about 1.5 to about 2.0 ($A_{peak}/A_{450}$).

Item 28. The composition according to any of items 25-27, wherein the threshold value is in range of about 0.7 to about 1.0 ($A_{peak}/A_{control}$).

Item 29. The composition according to any of items 25-28, wherein the concentration of the biopharmaceutical drug is in range of e.g. about 50 mg/mL to about 500 mg/mL, about 50 mg/mL to about 250 mg/mL, or about 100 mg/mL to about 250 mg/mL.

Item 30. A composition obtainable according to any of items 25-29 for use in medicine.

Item 31. A method according to any of items 1-24 for preparing a composition comprising a biopharmaceutical drug, wherein the composition has a viscosity from about 10-10.000 mPas, about 20-9000 mPas, about 30-8000 mPas, about 40-7000 mPas, about 50-6000 mPas, about 70-5000 mPas, about 90-4000 mPas, about 100-3000 mPas or about 10 mPas, or about 20 mPas, or about 30 mPas, or about 40 mPas, or about 50 mPas or alternatively from about 1 mPas to about 20 mPas, about 2 mPas, about 3 mPas, about 4 mPas, about 5 mPas, about 6 mPas, about 7 mPas, about 10 mPas, 13 mPas, 15 mP, or about 20 mPas.

Item 32. The method according to item 31, wherein the biopharmaceutical drug is one or more proteins or one or more antibodies or any mixtures thereof.

Item 33. The method according to any of items 31-32, wherein the antibody is a monoclonal antibody, or a polyclonal antibody, or a combination thereof.

Item 34. A bioanalytical mixture comprising:
a. at least two nanoparticles;
b. a protein in at least two phases; and
c. a salt or a buffer.

Item 35. The bioanalytical mixture of item 34, wherein the first of the at least two phases of the protein is a soluble phase.

Item 36. The bioanalytical mixture of item 34 or 35, wherein the second of the at least two phases of the protein is an adherent phase, wherein the protein is adhered to the surface of each of the at least two nanoparticles.

Item 37. The bioanalytical mixture according to any one of the preceding items 34 to 36, wherein the third of the at least two phases of the protein is an aggregated phase, wherein the protein is self-associated to form an aggregate.

Item 38. The bioanalytical mixture according to any one of the preceding items 34 to 37, wherein one or more of the aggregated protein is also adhered to the surface of a nanoparticle.

Item 39. The bioanalytical mixture according to any one of the preceding items 34 to 38, wherein each of the at least two nanoparticles comprises gold.

Item 40. The bioanalytical mixture according to any one of the preceding items 34 to 39, wherein each of the at least two nanoparticles comprises a diameter of about 20 nm to about 100 nm.

Item 41. The bioanalytical mixture according to any one of the preceding items 34 to 40, wherein the diameter is about 20 nm.

Item 42. The bioanalytical mixture according to any one of the preceding items 34 to 41, wherein each of the at least two nanoparticles is saturated with the protein.

Item 43. The bioanalytical mixture according to any one of the preceding items 34 to 42, wherein the nanoparticles are present at a density of about $6 \times 10^{11}$ to about $7 \times 10^{11}$ nanoparticles per milliliter of mixture.

Item 44. The bioanalytical mixture according to any one of the preceding items 34 to 43, wherein the protein is present at a concentration of about 2 μg/mL to about 512 μg/mL.

Item 45. The bioanalytical mixture according to any one of the preceding items 34 to 44, wherein the protein is an antigen-binding protein.

Item 46. The bioanalytical mixture according to any one of the preceding items 34 to 45, wherein the antigen-binding protein is selected from the group consisting of antibody, antibody fragment, aptamer and receptor-Fc-fusion protein.

Item 47. The bioanalytical mixture according to any one of the preceding items 34 to 46, wherein the antigen-binding protein is an antibody.

Item 48. The bioanalytical mixture according to any one of the preceding items 34 to 47, wherein the antibody is a human monoclonal antibody.

Item 49. The bioanalytical mixture according to any one of the preceding items 34 to 48, wherein the salt is present at a concentration of about 2 mM to about 300 mM.

Item 50. The bioanalytical mixture according to any one of the preceding items 34 to 49, wherein the salt is present at a concentration of about 2 mM, about 20 mM, or about 200 mM.

Item 51. The bioanalytical mixture according to any one of the preceding items 34 to 50, wherein the salt comprises NaCl.

EXAMPLES

The following examples are provided to further illustrate the methods of the present invention. These examples are illustrative only and are not intended to limit the scope of the invention in any way.

Example 1: Materials

The monoclonal antibodies (mAbs) were produced by EESYR® cells and purified by protein A chromatography and a polishing step of anion exchange or hydrophobic interaction chromatography. Buffer components were obtained from Sigma-Aldrich, VWR, or JT-Baker and were the highest grade available. Illustra NAP Columns (Cat. #17-0853-02) and a XK26/100 Superdex 200 pg column (Cat. #90-1002-73) were purchased from GE Healthcare Life Sciences.

Amicon Centrifugal Filter Units (Cat. #UFC905024) were purchased from EMD Millipore. Slide-A-Lyzer™ G2 Dialysis Cassettes (Cat. #87732) were purchased from ThermoFisher Scientific. 20 nm gold nanoparticles (Cat. #HD.GC20) was purchased from BBI solutions. Thermo Scientific™ Nunc™ Microwell™ 96-well microplates (Cat. #12-565-66) were used as the reaction container to acquire absorbance spectra.

Example 2: High Concentration Static Light Scattering (HC-SLS)

Concentrated (100 g/L) monoclonal antibodies (mAb1, mAb2, mAb3, mAb4, mAb5 and mAb6) were each purified on an Äkta avant (GE Healthcare Life Sciences) through a XK26/100 Superdex 200 pg column in 10 mM MES pH 6.0 50 mM sodium chloride. The monomer mAb fraction was collected and concentrated using an Easy-Load MAsterFlex L/S (Cole Parmer) pump in tandem with a VivaFlow 200 30,000 MWCO HY membrane. 150 mL of each concentrated antibody was split in to 3 fractions and loaded in to a 10,000 MWCO dialysis cassette and exchanged against 2 L of 10 mM MES pH 6.0, 250 mM sodium chloride; 10 mM MES pH 6.0, 50 mM sodium chloride; and 10 mM MES pH 6.0, 10 mM sodium chloride solutions. The solutions were concentrated, using a centrifugal filter unit with a 50,000 MWCO, to a final volume of approximately 15 mL in their respective buffers. The concentrations were measured using a SoloVPE (C Technologies, Inc.). Antibody could not be concentrated beyond nominally 60 g/L in 10 mM MES pH 6.0, 10 mM sodium chloride. The two other salt concentrations (250 mM and 50 mM sodium chloride) were adjusted to nominally 80 g/L. An aliquot from the three conditions were taken and diluted to 10 g/L. A sample of 80 g/L, 10 g/L and buffer were affixed to a CG-MALS device (Wyatt Technology) and the light scattering signal was measured as a function of mAb concentration.

Example 3: Standard Self-Interaction Nanoparticle Spectroscopy (SINS)

A sub-aliquot of each antibody (mAb1, mAb2, mAb3, mAb4, mAb5 and mAb6) under a different salt condition was added to a separate 15 mL falcon tube. 5 mL of one optical density (1 O.D.) of 20 nm gold nanoparticle solution was added to the solution so that the resultant final protein concentration was 50 µg/mL. The absorbance spectra and $\lambda_{max}$ were recorded on a SPECTRAmax 340PC (Molecular Devices) after waiting 30 minutes.

Concentration-dependent self-interaction nanoparticle spectroscopy (CD-SINS). 100 mM buffer solutions were prepared at the appropriate pH. Illustra NAP columns were conditioned with 2.4 mL of the 100 mM buffer solution (e.g. MES or sodium phosphate depending on the target pH). Concentrated (50-75 g/L) mAb stock solutions were buffer exchanged using the conditioned desalting column. The resultant concentration was measured using a SoloVPE. Each antibody was subsequently diluted to 5.12 mg/mL in 100 mM buffer. The mAb was then added to column 1 of the microwellplate and serially diluted in to 100 mM buffer down to 0.04 mg/mL. 80 µL of gold nanoparticles was added to columns 2, 3 and 4 of the 96 microwellplate. 40 µL of the serially diluted mAb was added to each column, using a multichannel pipette, containing the gold nanoparticles maintaining the serial dilution from column 1. 280 mL of 357 mM, 71 mM and 14 mM sodium chloride salt stock was subsequently added, using a multichannel pipette, to columns 2, 3 and 4 respectively. The resulting solution was allowed to equilibrate for 30 minutes before the absorbance spectra was recorded on a SPECTRAmax 340PC. The maximum absorbance intensity was normalized relative to the absorbance at 450 nm. This ratio is plotted as a function of the final concentration of the antibody.

Example 4: Dynamic Colloidal Stability of Human Serum Albumin (HSA)

Figure 4:
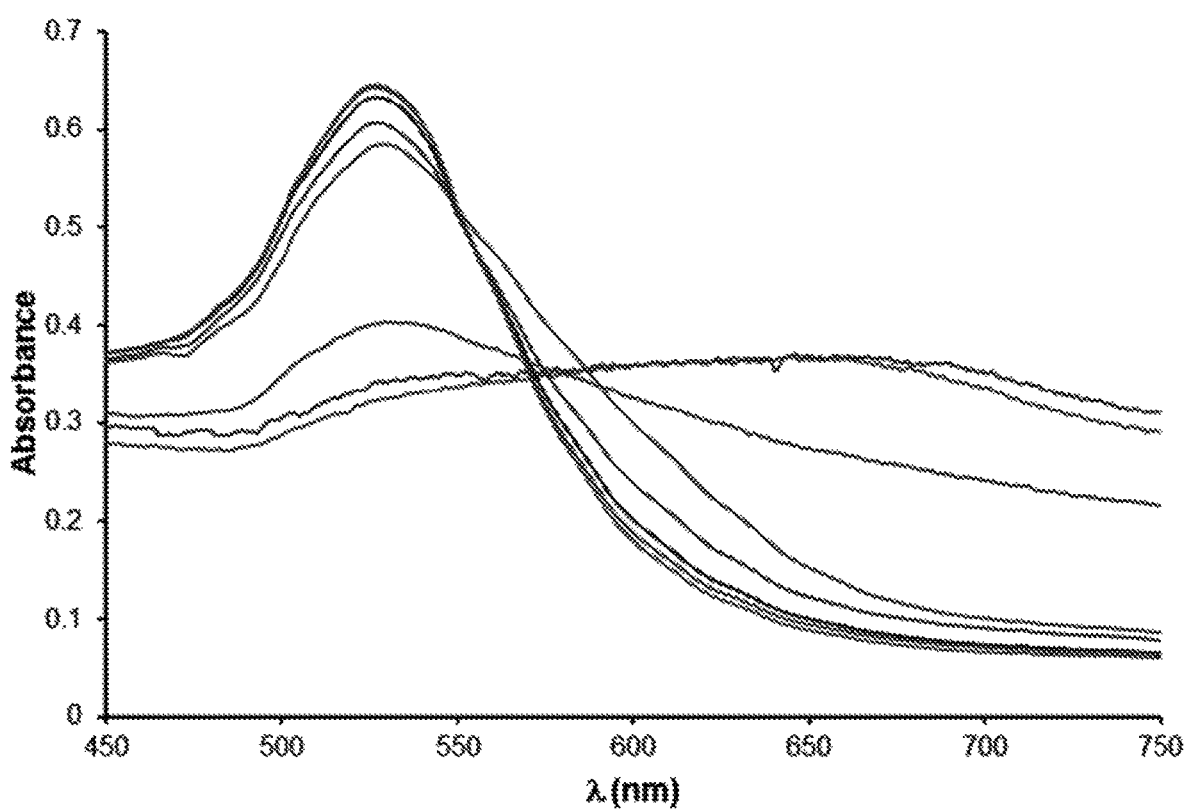
Figure 5:
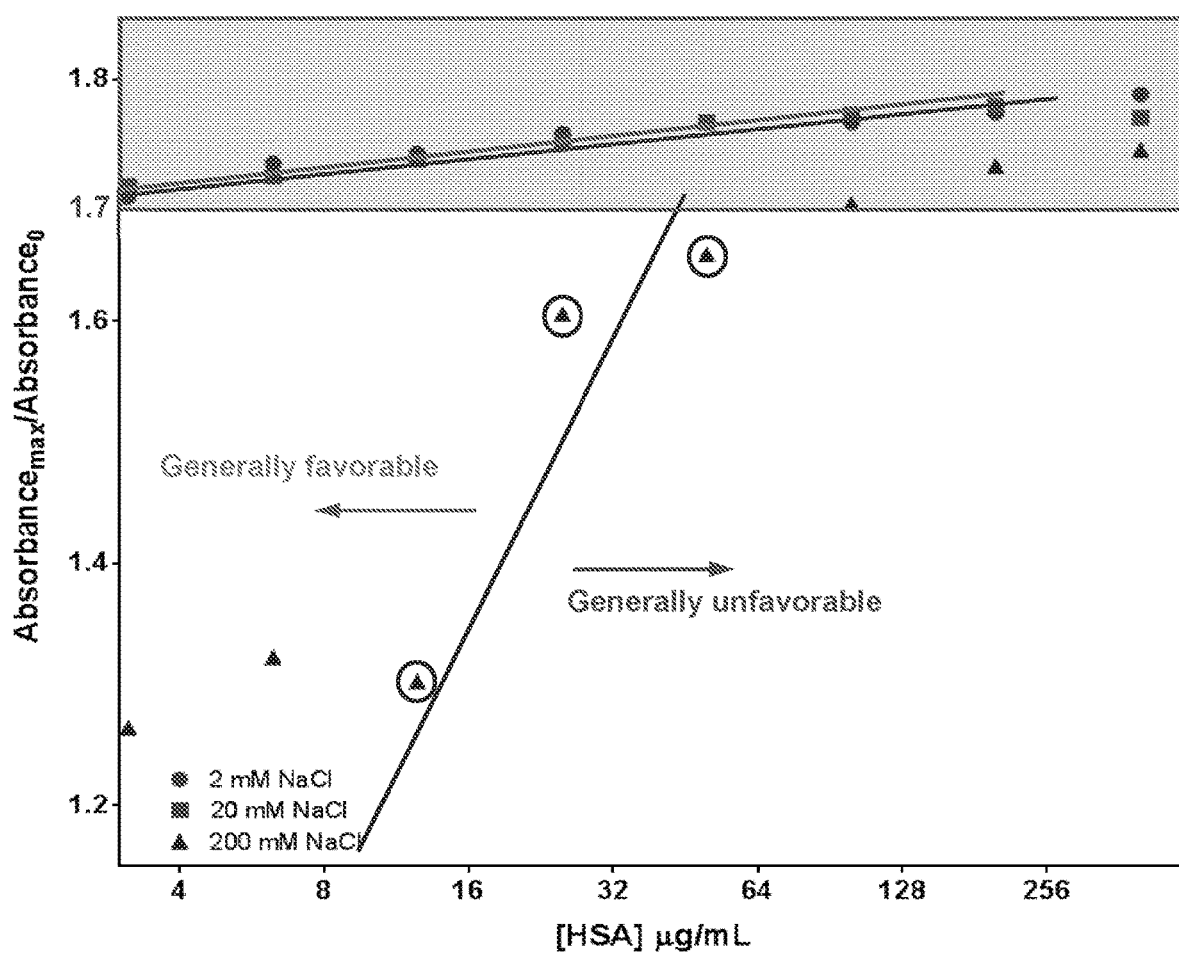

20 nm gold nanoparticles at about $6.3 \times 10^{11}$ particles per milliliter were combined with various concentrations of human serum albumin (HAS) in 10 mM MES buffer at 2 mM NaCl, 20 mM NaCl, or 200 mM NaCl, pH 6. Individual samples containing 3.125 µg/mL, 6.25 µg/mL, 12.5 µg/mL, 25 µg/mL, 50 µg/mL, 100 µg/mL, 200 µg/mL, and 400 µg/mL were subjected to absorbance spectroscopy. Those spectrograms were plotted (FIG. 4, depicts the spectra for the 200 mM NaCl samples) and the ratio of absorbance intensity at the maximum absorbance ($\lambda_{max}$) to the initial absorbance at 450 nm was calculated for each protein concentration and plotted (FIG. 5).

HSA shows an absorbance intensity ratio greater than 1.7 ($A_{peak}/A_{450}$) for all ionic strengths and at the higher protein concentrations, indicating a favorable dynamic colloidal interaction profile. Static light scattering experiments show positive virials ($A_2$) in overall agreement with the CD-SINS profile (Table 2).

TABLE 2

| NaCl mM | SLS ($A_2$) |
|---|---|
| 2 | 1.17E−4 |
| 20 | 9.68E−5 |
| 120 | 7.85E−5 |

Example 5: Monoclonal Antibody No. 1 (mAb1)

Figure 6:
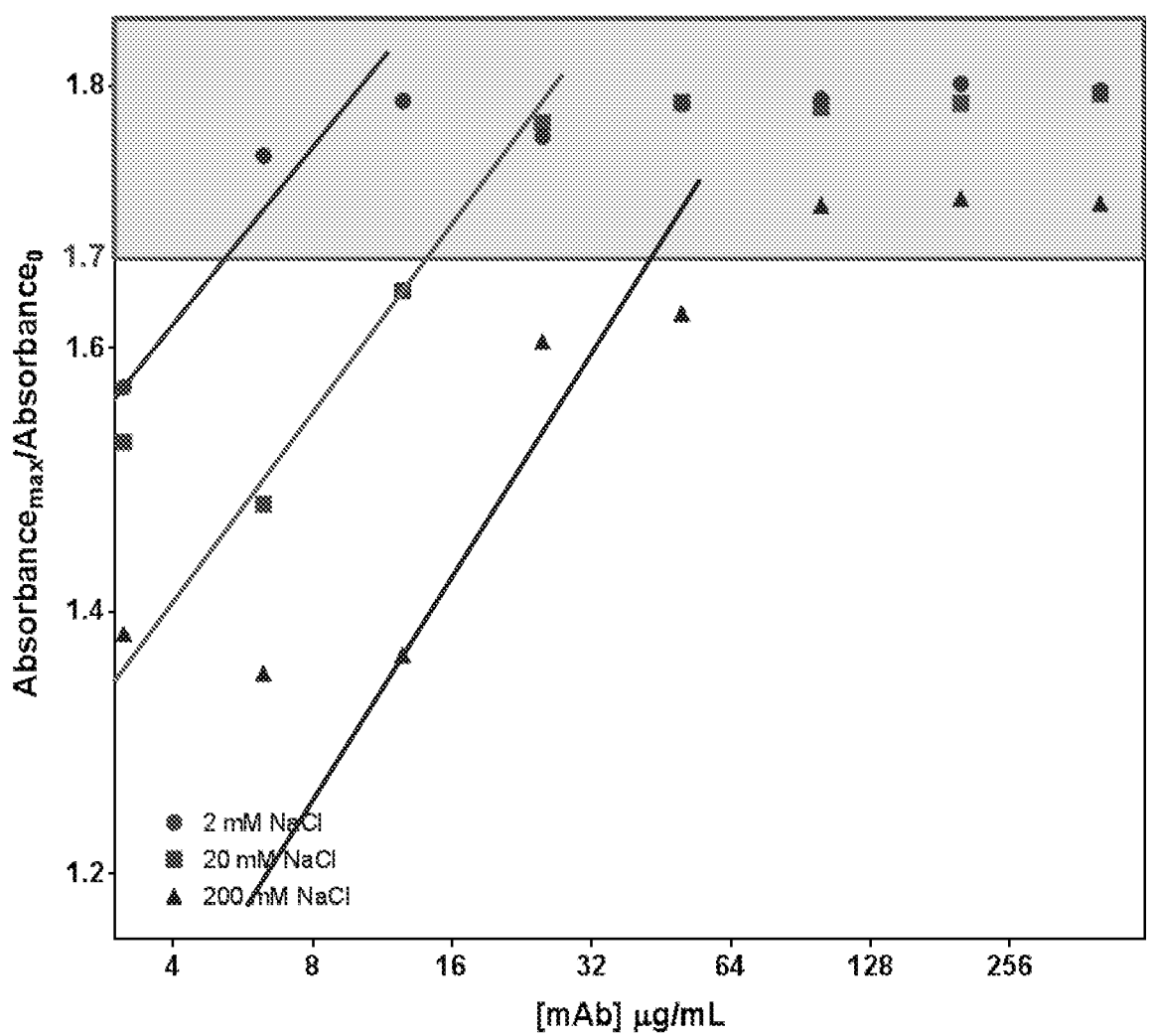
Figure 7:
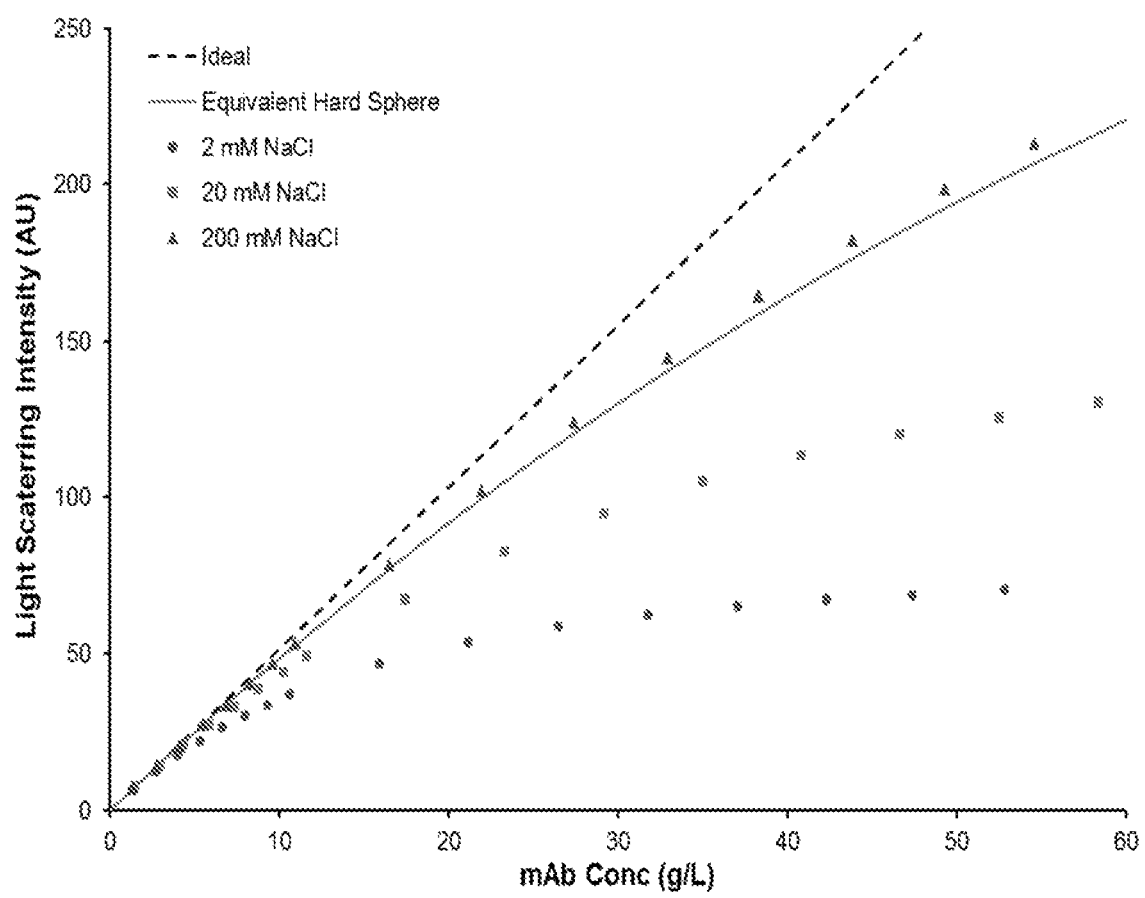

20 nm gold nanoparticles at about $6.3 \times 10^{11}$ particles per milliliter were combined with various concentrations of human mAb1 in 10 mM MES buffer at 2 mM NaCl, 20 mM NaCl, or 200 mM NaCl, pH 6. Individual samples containing 3.125 µg/mL, 6.25 µg/mL, 12.5 µg/mL, 25 µg/mL, 50 µg/mL, 100 µg/mL, 200 µg/mL, and 400 µg/mL were subjected to absorbance spectroscopy. Those spectrograms were plotted and the ratio of absorbance intensity at the maximum absorbance ($\lambda_{max}$) to the initial absorbance at 450 nm was calculated for each protein concentration and plotted (FIG. 6).

mAb1 shows an absorbance intensity ratio greater than 1.7 ($A_{peak}/A_{450}$) for all ionic strengths and at the higher protein concentrations, indicating a favorable dynamic colloidal interaction profile. High-concentration static light scattering experiments show positive virials ($A_2$) in overall agreement with the CD-SINS profile (Table 3, FIG. 7).

TABLE 3

| NaCl mM | SLS ($A_2$) |
| --- | --- |
| 2 | 1.72E−4 |
| 20 | 6.70E−5 |
| 200 | 1.34E−5 |

Example 6: Monoclonal Antibody No. 6 (mAb6)

Figure 8:
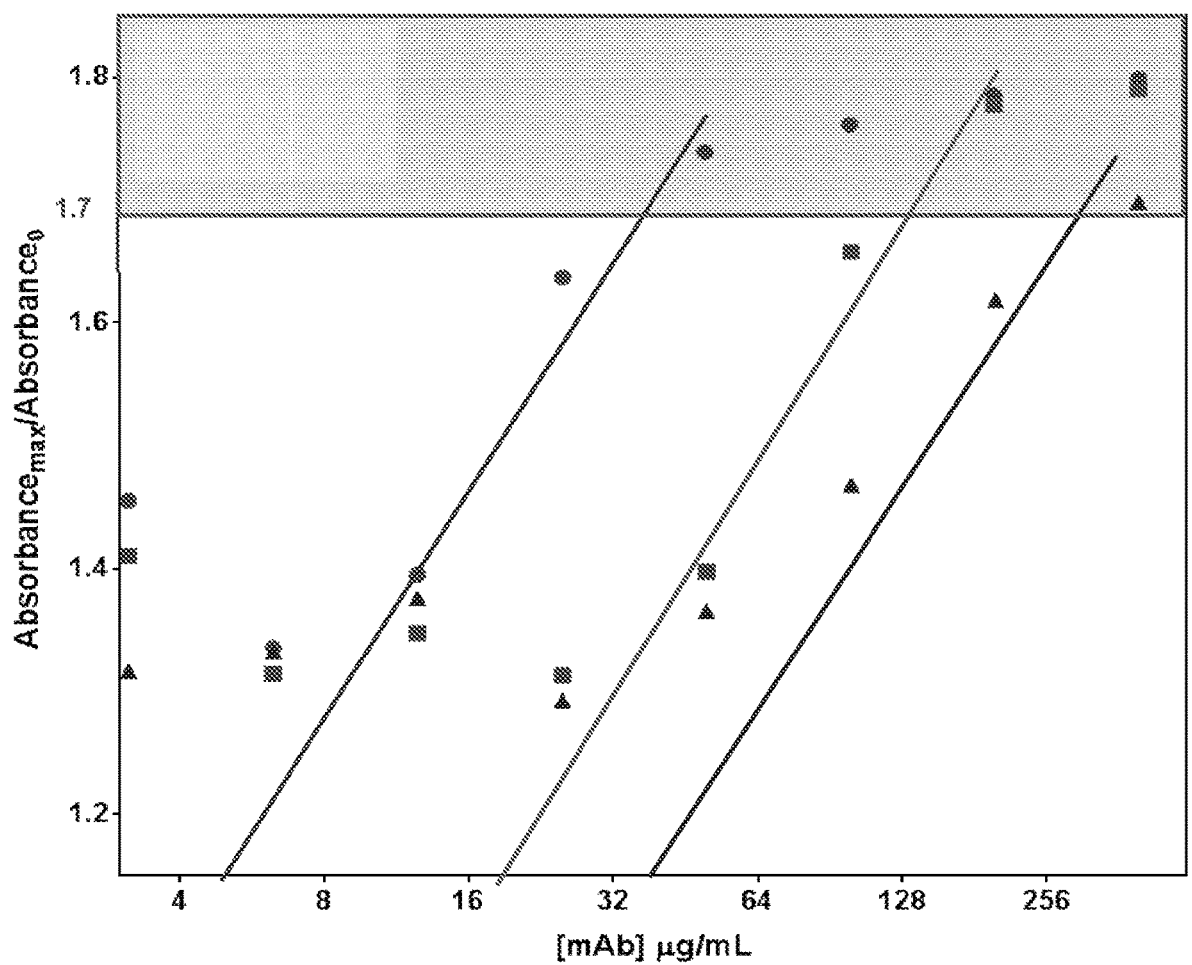
Figure 9:
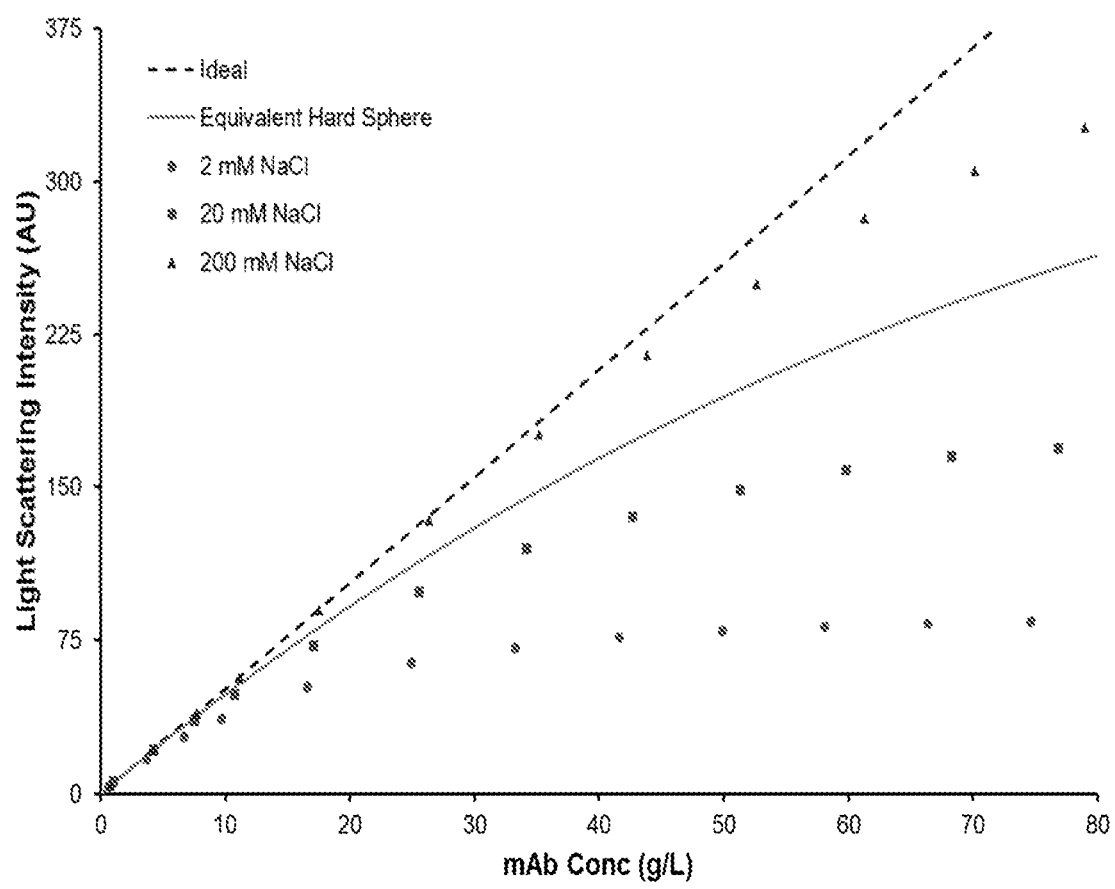

20 nm gold nanoparticles at about $6.3 \times 10^{11}$ particles per milliliter were combined with various concentrations of human mAb6 in 10 mM MES buffer at 2 mM NaCl, 20 mM NaCl, or 200 mM NaCl, pH 6. Individual samples containing 3.125 µg/mL, 6.25 µg/mL, 12.5 µg/mL, 25 µg/mL, 50 µg/mL, 100 µg/mL, 200 µg/mL, and 400 µg/mL were subjected to absorbance spectroscopy. Those spectrograms were plotted and the ratio of absorbance intensity at the maximum absorbance ($\lambda_{max}$) to the initial absorbance at 450 nm was calculated for each protein concentration and plotted (FIG. 8).

mAb6 shows an absorbance intensity ratio greater than 1.7 ($A_{peak}/A_{450}$) at the lower ionic strengths and at the higher protein concentrations, indicating a favorable dynamic colloidal interaction profile under those conditions. mAb6 exhibits an increase in attractive interactions with increasing ionic strength. High-concentration static light scattering experiments show variable virials ($A_2$) in overall agreement with the CD-SINS profile (FIG. 9).

Example 7: Monoclonal Antibody No. 2 (mAb2)

20 nm gold nanoparticles at about $6.3 \times 10^{11}$ particles per milliliter were combined with various concentrations of human mAb2 in 10 mM MES buffer at 2 mM NaCl, 20 mM NaCl, or 200 mM NaCl, pH 6. Individual samples containing 3.125 µg/mL, 6.25 µg/mL, 12.5 µg/mL, 25 µg/mL, 50 µg/mL, 100 µg/mL, 200 µg/mL, and 400 µg/mL were subjected to absorbance spectroscopy. Those spectrograms were plotted and the ratio of absorbance intensity at the maximum absorbance ($\lambda_{max}$) to the initial absorbance at 450 nm was calculated for each protein concentration and plotted (FIG. 2).

mAb2 shows profound changes in net protein interactions under varying conditions. At low ionic strength, mAb2 exhibits an increase in attractive interactions. The molecule becomes overall repulsive as the ionic strength increases. At 200 mM NaCl, the antibody has favorable colloidal stability. High-concentration static light scattering experiments show variable virials ($A_2$) in overall agreement with the conventional SINS wavelengths of maximum absorbance (Table 1).

Example 8: Monoclonal Antibody No. 3 (mAb3)

Figure 10:
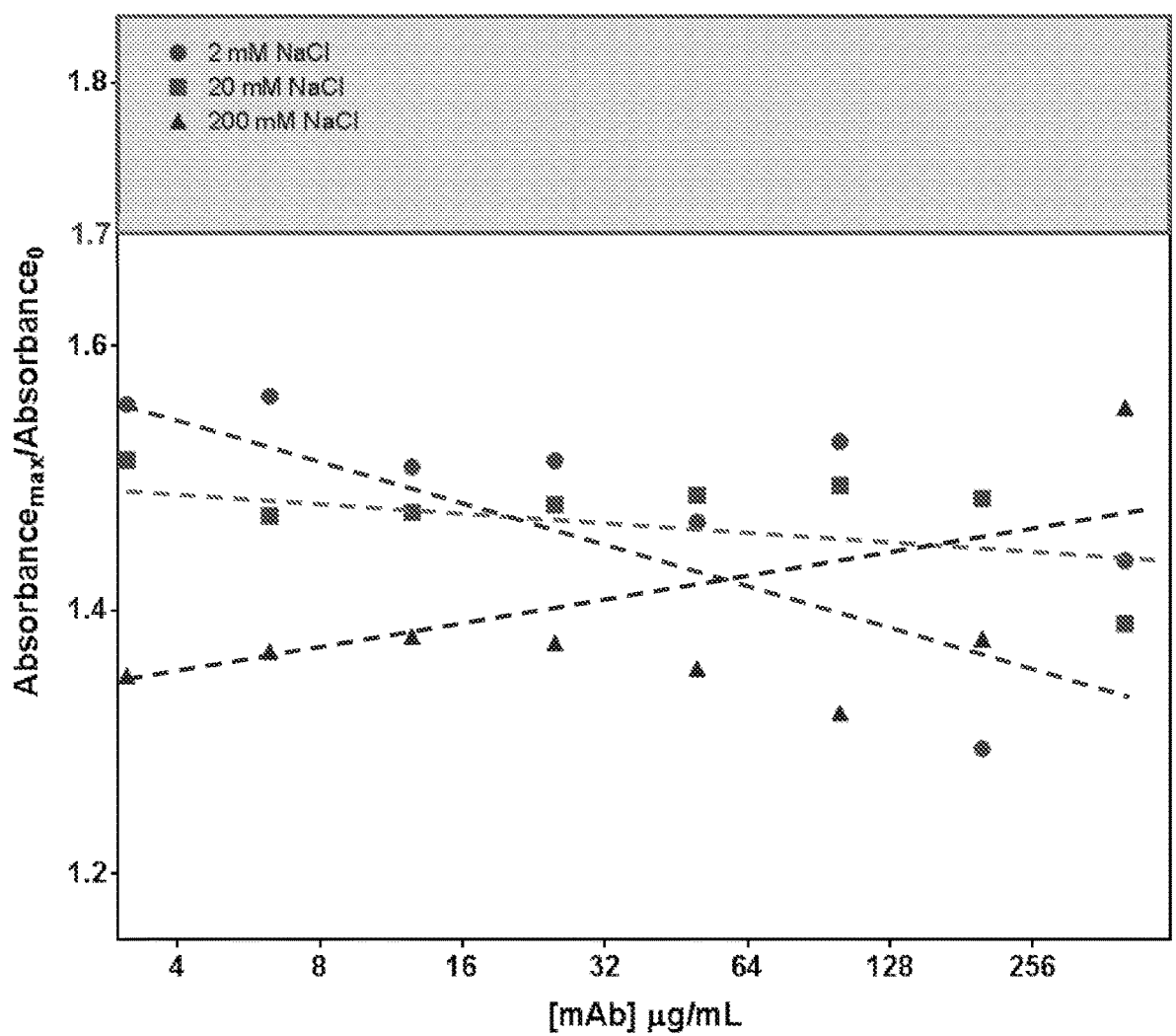

20 nm gold nanoparticles at about $6.3 \times 10^{11}$ particles per milliliter were combined with various concentrations of human mAb3 in 10 mM MES buffer at 2 mM NaCl, 20 mM NaCl, or 200 mM NaCl, pH 6. Individual samples containing 3.125 µg/mL, 6.25 µg/mL, 12.5 µg/mL, 25 µg/mL, 50 µg/mL, 100 µg/mL, 200 µg/mL, and 400 µg/mL were subjected to absorbance spectroscopy. Those spectrograms were plotted and the ratio of absorbance intensity at the maximum absorbance ($\lambda_{max}$) to the initial absorbance at 450 nm was calculated for each protein concentration and plotted (FIG. 10).

mAb3 is an example of a colloidally unstable protein that portends problematic high concentration formulation and manufacturing. At all ionic strengths and protein concentrations, mAb3 exhibits attractive interactions. High-concentration static light scattering experiments show negative virials ($A_2$) in overall agreement with the conventional SINS wavelengths of maximum absorbance (Table 1).

Example 9: Monoclonal Antibody No. 4 (mAb4)

Figure 11:
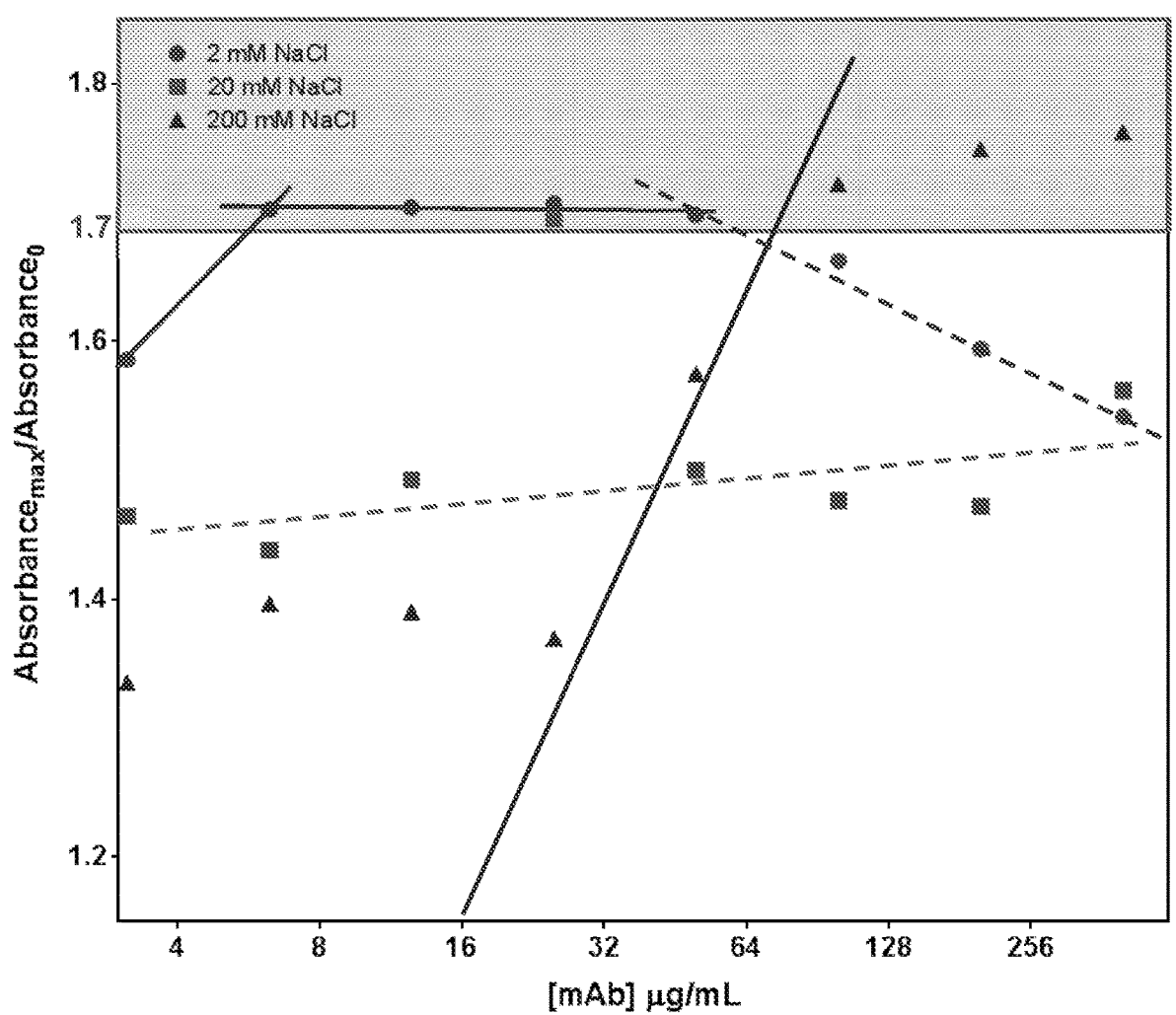

20 nm gold nanoparticles at about $6.3 \times 10^{11}$ particles per milliliter were combined with various concentrations of human mAb4 in 10 mM MES buffer at 2 mM NaCl, 20 mM NaCl, or 200 mM NaCl, pH 6. Individual samples containing 3.125 µg/mL, 6.25 µg/mL, 12.5 µg/mL, 25 µg/mL, 50 µg/mL, 100 µg/mL, 200 µg/mL, and 400 µg/mL were subjected to absorbance spectroscopy. Those spectrograms were plotted and the ratio of absorbance intensity at the maximum absorbance ($\lambda_{max}$) to the initial absorbance at 450 nm was calculated for each protein concentration and plotted (FIG. 11).

mAb4 is an example of a colloidally stable protein at lower ionic strengths, but showing less solubility at higher protein concentration in low ionic strength. Static light scattering experiments, which depict mixed virials (negative at lower ionic strength, positive at high ionic strength), show discrepancies with the CD-SINS-generated data, which shows a repulsive profile for mAb4 (Table 1).

Example 10: Monoclonal Antibody No. 5 (mAb5)

Figure 12:
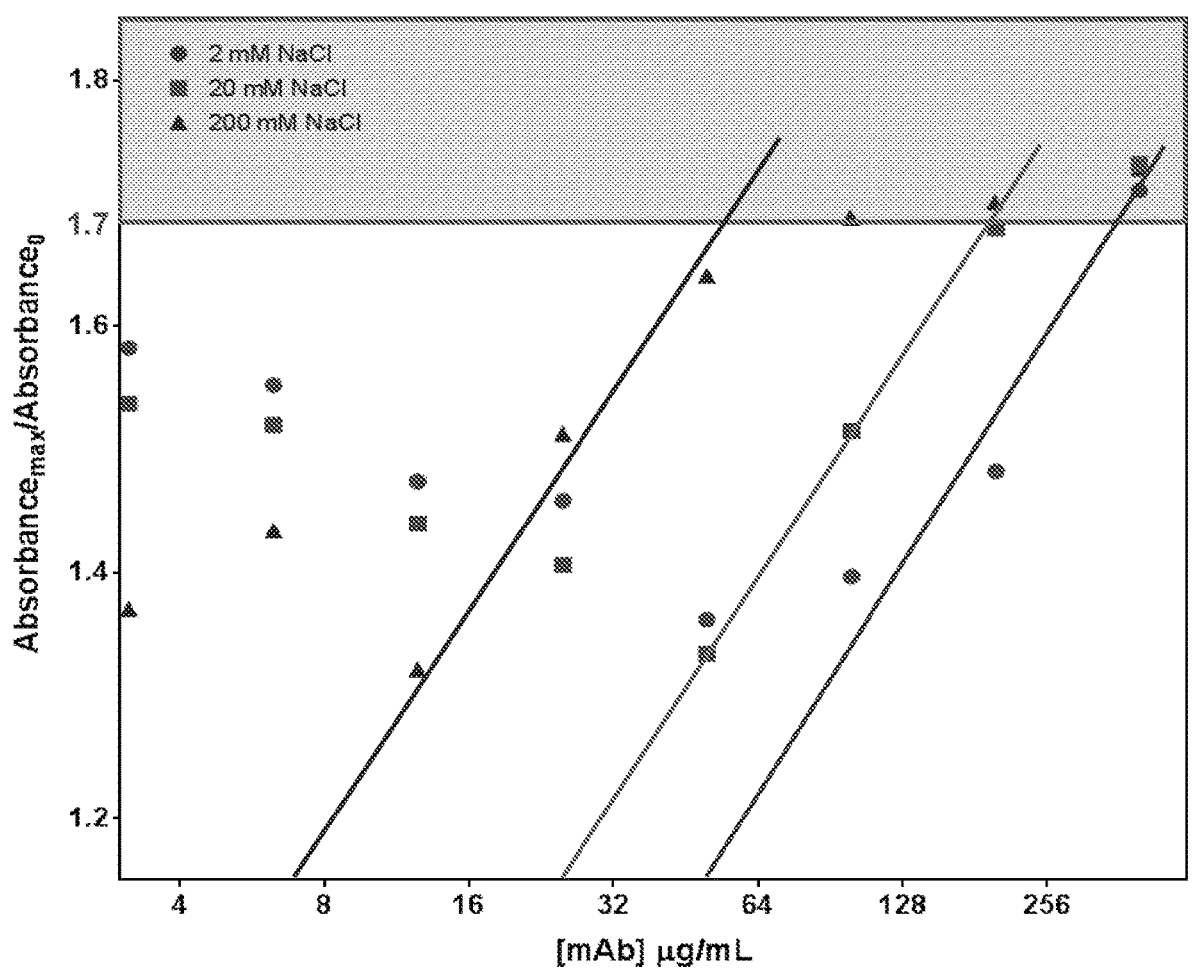

20 nm gold nanoparticles at about $6.3 \times 10^{11}$ particles per milliliter were combined with various concentrations of human mAb5 in 10 mM MES buffer at 2 mM NaCl, 20 mM NaCl, or 200 mM NaCl, pH 6. Individual samples containing 3.125 µg/mL, 6.25 µg/mL, 12.5 µg/mL, 25 µg/mL, 50 µg/mL, 100 µg/mL, 200 µg/mL, and 400 µg/mL were subjected to absorbance spectroscopy. Those spectrograms were plotted and the ratio of absorbance intensity at the maximum absorbance ($\lambda_{max}$) to the initial absorbance at 450 nm was calculated for each protein concentration and plotted (FIG. 12).

mAb5 is an example of a colloidally mixed protein that is attractive in low ionic strength and exhibits improvement in high protein concentration behavior with increasing ionic strength. Static light scattering experiments, which depict only negative virials, show discrepancies with the CD-SINS-generated data, which shows a mixed profile for mAb4 (Table 1).

Example 11: Excipient Screening and Selection

A high-viscosity formulated antibody having an unfavorable dynamic colloidal interaction profile under some formulation conditions (mAb7) was used to screen additional excipients for their ability to improve the antibody's CG-SINS profile. The CG-SINS profile of monoclonal antibody 7 (mAb7) formulated in various solutions containing different buffers and ionic strengths (FIG. 13), and sugar and/or amino acid excipients (FIG. 14) remained below the absorbance$_{max}$/absorbance$_0$ threshold value favorable for dispensing at high concentration (e.g., below 1.7). The viscosity of mAb7 formulated at about 100 mg/mL was observed at ~100 cP.

The CD-SINS assay was used to screen the colloidal stabilizing effect of various substituted benzoate compounds on mAb7. Substituted benzoic acids include m-hydroxybenzoic acid, ρ-hydroxybenzoic acid, m-methylbenzoic acid, ρ-methylbenzoic acid, m-ethylbenzoic acid, ρ-ethylbenzoic acid, m-aminobenzoic acid, ρ-aminobenzoic acid, a sulfonic acid, and an ammonium benzoate. FIG. 15 depicts the CD-SINS absorbance ratio scatter plot of mAb7 formulated with each of the substituted benzoic acids. When ρ-aminobenzoic acid (PABA, open circles in FIG. 15) was combined with the formulated mAb7, the mAb7 exhibited favorable colloidal stability as demonstrated by absorbance ratios over the threshold value favorable for dispersing at high concentration, i.e., >1.6 or 1.7 as depicted in FIG. 15.

PABA was combined in a dose dependent manner with mAb7 and subjected to CD-SINS analysis. The inclusion of >12 mM PABA (e.g., 18 Mm, 24 mM, 30 mM, and 36 mM PABA) with mAb7 produced a favorable (i.e., repulsive) colloidal interaction profile (FIG. 16). The effect of PABA on the colloidal interaction profile of mAb7 appeared to saturate at approximately 20 mM PABA.

20 mM PABA was combined with 5 g/L, 10 g/L, 30 g/L, 50 g/L, 70 g/L and 80 g/L of mAb7 and subjected to viscometric analysis using the cone and plate method using a torsional rheometer (Pathak et al., Biophys. J. 104(4): 913-923, 2013 Feb. 19). The results are depicted in FIG. 17. Extrapolation of those results to 100 g/L mAb7 using the Krieger-Dougherty algorithm (see, e.g., Lukham and Ukeje, J. Colloid Interface Sci., 220(2): 347-356, 1999 Dec. 15) showed an approximately three-fold reduction in steady shear viscosity in those mAb7 formulations containing 20 mM PABA.

What is claimed is:

1. A method for determining the potential of a protein to self-associate when it is at a high concentration, the method comprising:
   a. combining a protein at a low concentration, a nanoparticle, and a buffered salt to form a sample;
   b. exciting the sample with light;
   c. measuring the light transmitted through the sample at multiple wavelengths ranging from 450 nm to about 750 nm;
   d. calculating the absorbance intensity ratio of the sample, wherein the absorbance intensity ratio is the ratio of absorbance intensity at the maximum absorbance (λmax) to the initial absorbance at 450 nm;
   e. measuring the absorbance intensity ratio, and
   f. determining the protein retains 90% or more of its native structure at a high concentration when the absorbance intensity ratio exceeds 1.7.

2. The method of claim 1, wherein:
   (i) the protein is an antigen-binding protein;
   (ii) the protein is in the sample at the low concentration of about 2 µg/mL to about 512 µg/mL;
   (iii) the nanoparticle is a gold nanoparticle, wherein the gold nanoparticle has a diameter of about 20 nm to about 100 nm;
   (iv) the sample comprises about $5 \times 10^{11}$ to about $8 \times 10^{11}$ nanoparticles per mL; and/or
   (v) the salt is present in the sample at a concentration of about 2 mM to about 250 mM.

3. The method of claim 1 further comprising repeating steps (a)-(f) using a different concentration of protein in the sample.

4. The method of claim 1 further comprising repeating steps (a)-(f) using a different concentration of salt in the sample.

5. The method of claim 1 further comprising repeating steps (a)-(f) using a different pH of the sample.

6. The method of claim 1 further comprising:
   (g) combining the protein at a high concentration with an excipient to form a formulated drug substance or drug product.

7. The method of claim 6, wherein the concentration of the protein is about 50 mg/mL to about 500 mg/mL.

8. The method of claim 7, wherein the excipient is selected from the group consisting of a tonicifier, a buffer, a surfactant, stabilizer, and a combination thereof.

9. The method of claim 1, wherein the protein is present in the sample in a concentration in excess of a minimum concentration necessary to completely cover the nanoparticles.

10. The method of claim 1, wherein the protein is a receptor-Fc-fusion protein.

11. The method of claim 1, wherein the protein is an antibody or antibody fragment.

12. The method of claim 3, wherein the different protein concentrations include two or more protein concentrations from about 64 µg/mL to about 512 µg/mL.

13. The method of claim 1, wherein the protein is at a high concentration when it is present in a formulation at a concentration between about 50 mg/mL to about 500 mg/mL.

14. The method of claim 1, wherein the protein is at a high concentration when it is present in a formulation at a concentration between about 50 mg/mL to about 250 mg/mL.

15. The method of claim 1, wherein the nanoparticle is a gold nanoparticle that has a diameter of about 20 nm to about 100 nm.

16. The method of claim 1, wherein the sample comprises about $6 \times 10^{11}$ to about $6.5 \times 10^{11}$ nanoparticles per mL.

17. The method of claim 1, wherein:
   (i) the protein is in the sample at a concentration of about 2 µg/mL to about 512 µg/mL; and
   (ii) the protein is at a concentration when it is present in a formulation at a concentration between about 50 mg/mL to about 500 mg/mL.

18. The method of claim 1, wherein:
   (i) the protein is an antigen-binding protein, a receptor-Fc-fusion protein, an antibody, or antibody fragment;
   (ii) the protein is in the sample at a concentration of about 2 µg/mL to about 512 µg/mL;
   (iii) the nanoparticle is a gold nanoparticle that has a diameter of about 20 nm to about 100 nm;
   (iv) the sample comprises about $5 \times 10^{11}$ to about $8 \times 10^{11}$ nanoparticles per mL;
   (v) the salt is present in the sample at a concentration of about 2 mM to about 250 mM; and
   (vi) the protein is at a high concentration when it is present in a formulation at a concentration between about 50 mg/mL to about 500 mg/mL.

* * * * *